United States Patent
Dyer et al.

(10) Patent No.: US 7,807,023 B2
(45) Date of Patent: Oct. 5, 2010

(54) PROCESS FOR INCREASING THE BASIS WEIGHT OF SHEET MATERIALS

(75) Inventors: Thomas Joseph Dyer, Neenah, WI (US); Deborah Joy Nickel, Appleton, WI (US); Kenneth John Zwick, Neenah, WI (US); Mike T. Goulet, Neenah, WI (US); Jeffrey J. Timm, Menasha, WI (US); Perry H. Clough, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 118 days.

(21) Appl. No.: 11/818,504

(22) Filed: Jun. 14, 2007

(65) Prior Publication Data

US 2008/0041543 A1 Feb. 21, 2008

Related U.S. Application Data

(63) Continuation-in-part of application No. 11/303,002, filed on Dec. 15, 2005, and a continuation-in-part of application No. 11/304,490, filed on Dec. 15, 2005, and a continuation-in-part of application No. 11/303,036, filed on Dec. 15, 2005, and a continuation-in-part of application No. 11/304,998, filed on Dec. 15, 2005, and a continuation-in-part of application No. 11/304,063, filed on Dec. 15, 2005, and a continuation-in-part of application No. 11/635,385, filed on Dec. 7, 2006.

(51) Int. Cl.
*D21H 17/34* (2006.01)
*B31F 1/12* (2006.01)
*D21H 23/22* (2006.01)
*D21H 23/56* (2006.01)

(52) U.S. Cl. .............. 162/168.1; 162/111; 162/112; 162/135; 162/158; 162/164.1

(58) Field of Classification Search .......... 162/112, 162/158, 164.1, 168.1, 184
See application file for complete search history.

(56) References Cited

U.S. PATENT DOCUMENTS 3,338,992 A 8/1967 Kinney
(Continued)

FOREIGN PATENT DOCUMENTS

CA 2273912 7/1998
DE 41 42 460 A1 6/1993
(Continued)

OTHER PUBLICATIONS

Smook, Gary A., Handbook for Pulp and Paper Technologists, 2nd ed, Angus Wilde Publications, 1992, p. 324.*
(Continued)

*Primary Examiner*—Eric Hug
*Assistant Examiner*—Dennis Cordray
(74) *Attorney, Agent, or Firm*—Dority & Manning, P.A.

(57) ABSTRACT

Sheet-like products are disclosed containing an additive composition. In accordance with the present disclosure, the additive composition is applied to a creping surface. A base sheet is then pressed against the creping surface for contact with the additive composition. The base sheet is then creped from the creping surface causing the additive composition to transfer to the base sheet. In particular, the additive composition is transferred to the base sheet in amounts greater than about 1% by weight, such as from about 2% to about 50% by weight. The additive composition can comprise, for instance, a thermoplastic polymer resin containing an aqueous dispersion, a lotion, a debonder, a softener, or mixtures thereof.

50 Claims, 16 Drawing Sheets

U.S. PATENT DOCUMENTS

| | | | |
|---|---|---|---|
| 3,341,394 A | 9/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,556,932 A | 1/1971 | Coscia et al. | |
| 3,556,933 A | 1/1971 | Williams et al. | |
| 3,575,173 A | 4/1971 | Loyer | |
| 3,585,104 A | 6/1971 | Kleinert | |
| 3,645,992 A | 2/1972 | Elston | |
| 3,669,822 A | 6/1972 | Cowen | |
| 3,692,618 A | 9/1972 | Dorschner et al. | |
| 3,700,623 A | 10/1972 | Keim | |
| 3,772,076 A | 11/1973 | Keim | |
| 3,802,817 A | 4/1974 | Matsuki et al. | |
| 3,812,000 A * | 5/1974 | Yiannos et al | 162/111 |
| 3,849,241 A | 11/1974 | Butin et al. | |
| 3,855,158 A | 12/1974 | Petrovich et al. | |
| 3,879,257 A | 4/1975 | Gentile et al. | |
| 3,899,388 A | 8/1975 | Petrovich et al. | |
| 4,076,698 A | 2/1978 | Anderson et al. | |
| 4,100,324 A | 7/1978 | Anderson et al. | |
| 4,129,528 A | 12/1978 | Petrovich et al. | |
| 4,147,586 A | 4/1979 | Petrovich et al. | |
| 4,222,921 A | 9/1980 | Van Eenam | |
| 4,309,510 A | 1/1982 | Kleber | |
| 4,326,000 A | 4/1982 | Roberts, Jr. | |
| 4,340,563 A | 7/1982 | Appel et al. | |
| 4,355,066 A | 10/1982 | Newman | |
| 4,375,448 A | 3/1983 | Appel et al. | |
| 4,440,898 A | 4/1984 | Pomplun et al. | |
| 4,494,278 A | 1/1985 | Kroyer et al. | |
| 4,514,345 A | 4/1985 | Johnson et al. | |
| 4,528,239 A | 7/1985 | Trokhan | |
| 4,574,021 A | 3/1986 | Endres et al. | |
| 4,594,130 A | 6/1986 | Chang et al. | |
| 4,599,392 A | 7/1986 | McKinney et al. | |
| 4,640,810 A | 2/1987 | Laursen et al. | |
| 4,793,898 A | 12/1988 | Laamanen et al. | |
| 4,818,464 A | 4/1989 | Lau | |
| 4,837,070 A | 6/1989 | Weber et al. | |
| 4,878,299 A * | 11/1989 | Wedel | 34/513 |
| 4,950,545 A | 8/1990 | Walter et al. | |
| 4,975,320 A | 12/1990 | Goldstein et al. | |
| 4,988,781 A | 1/1991 | McKinney et al. | |
| 5,008,344 A | 4/1991 | Bjorkquist | |
| 5,085,736 A | 2/1992 | Bjorkquist | |
| 5,098,522 A | 3/1992 | Smurkoski et al. | |
| 5,104,923 A | 4/1992 | Steinwand et al. | |
| 5,109,063 A | 4/1992 | Cheng et al. | |
| 5,129,988 A | 7/1992 | Farrington, Jr. | |
| 5,160,484 A | 11/1992 | Nikoloff | |
| 5,227,242 A | 7/1993 | Walter et al. | |
| 5,260,171 A | 11/1993 | Smurkoski et al. | |
| 5,272,236 A | 12/1993 | Lai et al. | |
| 5,275,700 A | 1/1994 | Trokhan | |
| 5,278,272 A | 1/1994 | Lai et al. | |
| 5,328,565 A | 7/1994 | Rasch et al. | |
| 5,334,289 A | 8/1994 | Trokhan et al. | |
| 5,382,400 A | 1/1995 | Pike et al. | |
| 5,384,373 A | 1/1995 | McKinney et al. | |
| 5,385,643 A | 1/1995 | Ampulski | |
| 5,389,202 A | 2/1995 | Everhart et al. | |
| 5,389,204 A | 2/1995 | Ampulski | |
| 5,429,686 A | 7/1995 | Chiu et al. | |
| 5,431,786 A | 7/1995 | Rasch et al. | |
| 5,432,000 A | 7/1995 | Young et al. | |
| 5,496,624 A | 3/1996 | Stelljes, Jr. et al. | |
| 5,500,277 A | 3/1996 | Trokhan et al. | |
| 5,514,523 A | 5/1996 | Trokhan et al. | |
| 5,518,585 A | 5/1996 | Huth et al. | |
| 5,527,171 A | 6/1996 | Soerensen | |
| 5,529,665 A | 6/1996 | Kaun | |
| 5,543,215 A | 8/1996 | Hansen et al. | |
| 5,554,467 A | 9/1996 | Trokhan et al. | |
| 5,558,873 A | 9/1996 | Funk et al. | |
| 5,566,724 A | 10/1996 | Trokhan et al. | |
| 5,573,637 A | 11/1996 | Ampulski et al. | |
| 5,595,628 A | 1/1997 | Gordon et al. | |
| 5,624,790 A | 4/1997 | Trokhan et al. | |
| 5,628,876 A | 5/1997 | Ayers et al. | |
| 5,656,132 A | 8/1997 | Farrington, Jr. et al. | |
| 5,672,248 A | 9/1997 | Wendt et al. | |
| 5,677,383 A | 10/1997 | Chum et al. | |
| 5,830,320 A | 11/1998 | Park et al. | |
| 5,844,045 A | 12/1998 | Kolthammer et al. | |
| 5,869,575 A | 2/1999 | Kolthammer et al. | |
| 5,871,763 A | 2/1999 | Luu et al. | |
| 5,885,697 A | 3/1999 | Krzysik et al. | |
| 5,935,384 A | 8/1999 | Taniguchi | |
| 6,033,761 A | 3/2000 | Dwiggins et al. | |
| 6,054,020 A | 4/2000 | Goulet et al. | |
| 6,096,152 A | 8/2000 | Anderson et al. | |
| 6,096,169 A | 8/2000 | Hermans et al. | |
| 6,111,023 A | 8/2000 | Chum et al. | |
| 6,120,642 A | 9/2000 | Lindsay et al. | |
| 6,129,815 A | 10/2000 | Larson et al. | |
| 6,143,135 A | 11/2000 | Hada et al. | |
| 6,171,441 B1 | 1/2001 | Phillips et al. | |
| 6,194,517 B1 | 2/2001 | Pomplun et al. | |
| 6,197,154 B1 | 3/2001 | Chen et al. | |
| 6,224,714 B1 | 5/2001 | Schroeder et al. | |
| 6,231,719 B1 | 5/2001 | Garvey et al. | |
| 6,274,667 B1 | 8/2001 | Shannon et al. | |
| 6,287,418 B1 | 9/2001 | Schroeder et al. | |
| 6,291,372 B1 | 9/2001 | Mumick et al. | |
| 6,316,549 B1 | 11/2001 | Chum et al. | |
| 6,361,784 B1 | 3/2002 | Brennan et al. | |
| 6,365,667 B1 | 4/2002 | Shannon et al. | |
| 6,379,498 B1 | 4/2002 | Burns et al. | |
| 6,423,270 B1 | 7/2002 | Wall | |
| 6,447,643 B2 | 9/2002 | Fingal et al. | |
| 6,448,341 B1 | 9/2002 | Kolthammer et al. | |
| 6,538,070 B1 | 3/2003 | Cardwell et al. | |
| 6,566,446 B1 | 5/2003 | Parikh et al. | |
| 6,570,054 B1 | 5/2003 | Gatto et al. | |
| 6,617,490 B1 | 9/2003 | Chen et al. | |
| 6,716,203 B2 | 4/2004 | Sorebo et al. | |
| 6,764,988 B2 | 7/2004 | Koenig et al. | |
| 6,808,595 B1 * | 10/2004 | Burns et al. | 162/9 |
| 6,908,966 B2 | 6/2005 | Chang et al. | |
| 6,911,573 B2 | 6/2005 | Chen et al. | |
| 6,913,673 B2 | 7/2005 | Baggot et al. | |
| 6,951,598 B2 | 10/2005 | Flugge et al. | |
| 6,991,706 B2 | 1/2006 | Lindsay et al. | |
| 6,994,865 B2 | 2/2006 | Branham et al. | |
| 2002/0103469 A1 | 8/2002 | Chen | |
| 2002/0115744 A1 | 8/2002 | Svenningsen et al. | |
| 2002/0162243 A1 | 11/2002 | Runge et al. | |
| 2003/0027470 A1 | 2/2003 | Cheng et al. | |
| 2003/0072950 A1 | 4/2003 | Rodrigues et al. | |
| 2003/0121627 A1 | 7/2003 | Hu et al. | |
| 2004/0020114 A1 | 2/2004 | Boehmer et al. | |
| 2004/0084165 A1 | 5/2004 | Shannon et al. | |
| 2004/0099388 A1 | 5/2004 | Chen et al. | |
| 2004/0099389 A1 | 5/2004 | Chen et al. | |
| 2004/0118532 A1 | 6/2004 | Sarbo et al. | |
| 2004/0118540 A1 | 6/2004 | Garnier et al. | |
| 2004/0191486 A1 | 9/2004 | Underhill et al. | |
| 2004/0209539 A1 | 10/2004 | Confalone et al. | |
| 2004/0234804 A1 | 11/2004 | Liu et al. | |
| 2005/0010075 A1 | 1/2005 | Powers | |
| 2005/0045292 A1 | 3/2005 | Lindsay | |
| 2005/0045294 A1 | 3/2005 | Goulet et al. | |
| 2005/0045295 A1 | 3/2005 | Goulet et al. | |

| | | | |
|---|---|---|---|
| 2005/0058693 A1 | 3/2005 | Joseph et al. | |
| 2005/0058833 A1 | 3/2005 | Krzysik et al. | |
| 2005/0100754 A1 | 5/2005 | Moncla et al. | |
| 2005/0118435 A1 | 6/2005 | Delucia et al. | |
| 2005/0124753 A1 | 6/2005 | Ashihara et al. | |
| 2005/0136766 A1 | 6/2005 | Tanner et al. | |
| 2005/0148257 A1 | 7/2005 | Hermans et al. | |
| 2005/0192365 A1 | 9/2005 | Strandburg et al. | |
| 2005/0214335 A1 | 9/2005 | Allen et al. | |
| 2005/0217814 A1 | 10/2005 | Super et al. | |
| 2005/0224200 A1 | 10/2005 | Bouchard et al. | |
| 2005/0241789 A1 | 11/2005 | Reddy | |
| 2006/0014884 A1 | 1/2006 | Goulet et al. | |
| 2006/0070712 A1 | 4/2006 | Runge et al. | |
| 2006/0085998 A1 | 4/2006 | Herman et al. | |
| 2006/0086472 A1 | 4/2006 | Hermans et al. | |
| 2007/0020315 A1 | 1/2007 | Shannon et al. | |
| 2007/0137808 A1 | 6/2007 | Lostocco et al. | |
| 2007/0137809 A1 | 6/2007 | Dyer et al. | |
| 2007/0137810 A1 | 6/2007 | Dyer et al. | |
| 2007/0137811 A1 | 6/2007 | Runge et al. | |
| 2007/0137813 A1 | 6/2007 | Nickel et al. | |
| 2007/0141936 A1 | 6/2007 | Bunyard et al. | |
| 2007/0144697 A1 | 6/2007 | Dyer et al. | |
| 2007/0295464 A1 | 12/2007 | Fetner et al. | |
| 2008/0000598 A1 | 1/2008 | Dyer et al. | |
| 2008/0000602 A1 | 1/2008 | Dyer et al. | |
| 2008/0041543 A1 | 2/2008 | Dyer et al. | |
| 2008/0073045 A1 | 3/2008 | Dyer et al. | |
| 2008/0073046 A1 | 3/2008 | Dyer et al. | |
| 2008/0135195 A1 | 6/2008 | Hermans et al. | |

FOREIGN PATENT DOCUMENTS

| | | | |
|---|---|---|---|
| EP | 0608460 A1 | 1/1993 | |
| EP | 0620256 A2 | 3/1994 | |
| EP | 0857453 A1 | 8/1998 | |
| EP | 0926288 B1 | 6/1999 | |
| EP | 1344511 A2 | 9/2003 | |
| GB | 142441 | 3/1921 | |
| GB | 2246373 A | 1/1992 | |
| WO | WO 9501479 A1 | 1/1995 | |
| WO | WO 97/33921 | 9/1997 | |
| WO | WO 9934057 A1 | 7/1999 | |
| WO | WO 0066835 A1 | 11/2000 | |
| WO | WO 0147699 | 7/2001 | |
| WO | WO 0149933 | 7/2001 | |
| WO | WO 0248458 A1 | 6/2002 | |
| WO | WO 03040442 A1 | 5/2003 | |
| WO | WO 2005021622 A2 | 3/2005 | |
| WO | WO 2005021638 A2 | 3/2005 | |
| WO | WO 2005031068 A1 | 4/2005 | |
| WO | WO 2005080677 A2 | 9/2005 | |
| WO | WO 2006/038977 | 4/2006 | |
| WO | WO 2007/070114 | 6/2007 | |
| WO | WO 2007/070145 | 6/2007 | |
| WO | WO 2007070129 A1 | 6/2007 | |
| WO | WO 2007070145 A1 | 6/2007 | |
| WO | WO 2007070153 A1 | 6/2007 | |
| WO | WO 2007075356 A1 | 7/2007 | |
| WO | WO 2007078342 A1 | 7/2007 | |
| WO | WO 2007078499 A1 | 7/2007 | |

OTHER PUBLICATIONS

ASTM Designation: D 1238—04c entitled Standard Test Method for Melt Flow Rates of Thermoplastics by Extrusion Plastometer, Dec. 1, 2004, pp. 1-14.

ASTM Designation: D 792—98 entitled Standard Test Method for Density and Specific Gravity (Relative Density) of Plastics by Displacement, Aug. 10, 1998, pp. 159-163.

Material Safety Data Sheet from DuPont Dow Elastomers L. L. C., for "ENGAGE", Mar. 29, 1999, 7 pages.

Paper entitled "Polymer Nanocomposite" by Chou et al. of The Dow Chemical Company, 2002, 5 pages.

Product Information for Affinity EG 8200 (Polyolefin Plastomer for General Plastomeric Applications) from The Dow Chemical Company, May 2001, 2 pages.

TAPPI—T 411 om-89 entitled "Thickness (caliper) of paper, paperboard, and combined board", Jun. 15, 1989, 3 pages.

Search Report for Int'l Appl. No. PCT/US2006/037844 mailed Feb. 1, 2007.

Search Report and Written Opinion for PCT/US2006/033227, Jun. 5, 2007.

Search Report and Written Opinion for PCT/US2006/047785, Oct. 5, 2007.

Search Report and Written Opinion for PCT/US2006/038991, Feb. 9, 2007.

Search Report and Written Opinion for PCT/US2006/033224, Dec. 27, 2006.

Search Report and Written Opinion for PCT/IB2007/054405, completed Feb. 28, 2008.

U.S. Appl. No. 11/635,379, filed Dec. 7, 2006 entitled "Process for Producing Tissue Products".

International Search Report and Written Opinion, PCT/IB2007/054652, Jul. 30, 2008.

International Search Report and Written Opinion, PCT/IB2007/054651, Jul. 30, 2008.

International Search Report and Written Opinion, PCT/IB2007/054367, Jul. 30, 2008.

Search Report and Written Opinion for PCT/IB2007/046062 dated May 3, 2007.

Search Report and Written Opinion for PCT/IB2007/054404 dated May 21, 2008.

* cited by examiner

Control Sample at 500x magnification.

6.8% by weight of the additive composition at 500x magnification.

13% by weight of the additive composition at 500x magnification.

SEM surface image, magnification = 15X

SEM surface image, magnification = 30X

SEM surface image, magnification = 15X

SEM surface image, magnification = 30X

SEM surface image, magnification = 150X

SEM surface image, magnification = 750X

PROCESS FOR INCREASING THE BASIS WEIGHT OF SHEET MATERIALS

RELATED APPLICATIONS

The present application claims priority to and is a continuation-in-part application of U.S. Ser. No. 11/303,002 filed on Dec. 15, 2005, U.S. Ser. No. 11/304,490 filed on Dec. 15, 2005, U.S. Ser. No. 11/303,036 filed on Dec. 15, 2005, U.S. Ser. No. 11/304,998 filed on Dec. 15, 2005, U.S. Ser. No. 11/304,063 filed on Dec. 15, 2005 and U.S. Ser. No. 11/635,385 filed on Dec. 7, 2006.

BACKGROUND

Absorbent tissue products such as paper towels, facial tissues, bath tissues and other similar products are designed to include several important properties. For example, the products should have good bulk, a soft feel and should be highly absorbent. In addition, the products should also have sufficient strength for the particular application and environment in which they are to be used.

In the past, those skilled in the art have developed various processes for enhancing and improving various properties of tissue products. For example, in order to increase bulk and improve softness, tissue products have been subjected to creping processes. For example, in one embodiment, a creping adhesive is sprayed onto a rotating drum, such as a Yankee dryer. A tissue web is then adhered to the outside surface as the drum is rotating. A creping blade is then used to remove the tissue web from the surface of the drum. Creping the web from the drum compacts the web and can break fiber to fiber bonds which both increases the bulk and softness of the product.

The present disclosure is directed to further improvements in web creping processes. In particular, the present disclosure is directed to process that can not only be used to crepe base sheets but can also be used to incorporate useful additives into the base sheets in amounts sufficient to improve the properties of the sheets.

SUMMARY

In general, the present disclosure is directed to a method for applying an additive composition to a base sheet. In addition, as will be described in greater detail below, the base sheet may also be subjected to a creping process while the additive composition is being applied to the base sheet. Of particular advantage, the additive composition can be applied to the base sheet according to the present disclosure in an amount sufficient so as to increase the basis weight of the base sheet and improve various properties of the sheet.

For instance, in one embodiment, the present disclosure is directed to a process for producing a sheet product. The process includes the steps of applying an additive composition to a moving creping surface. The creping surface, for instance, may comprise the surface of a rotating drum. The drum may be at ambient temperature or may be heated.

Once the additive composition is applied to the creping surface, a base sheet is pressed against the creping surface. The additive composition adheres the base sheet to the creping surface. The base sheet is then removed from the creping surface. For instance, in one embodiment, a creping blade can be used to crepe the base sheet from the creping surface. During removal of the base sheet from the creping surface, in accordance with the present disclosure, the additive composition transfers to the base sheet such that the basis weight of the base sheet increases by at least about 1% by weight. Thus, the additive composition not only adheres the base sheet to the creping surface, but also transfers to the base sheet in an amount sufficient to influence the basis weight.

For example, through the process of the present disclosure, the basis weight of the base sheet may increase in an amount of at least 1% by weight, such as from about 1% to about 50% by weight, such as from about 1% to about 40% by weight, such as from about 1% to about 30% by weight, such as from about 2% to about 15% by weight. The basis weight of the base sheet, for instance, may increase in an amount of at least about 2% by weight, such as at least about 3% by weight, such as at least about 4% by weight, such as at least about 5% by weight, such as at least about 6% by weight. In one embodiment, for instance, the basis weight of the base sheet may increase in an amount from about 5% to about 10% by weight.

In accordance with the present disclosure, the additive composition may comprise any suitable composition capable of adhering the base sheet to the creping surface while also being capable of transferring to the base sheet after the base sheet is removed from the creping surface. The additive composition can comprise, for instance, a thermoplastic polymer, such as a dispersion containing a thermoplastic polymer. In other embodiments, the additive composition may comprise a lotion, a softener, a debonder for cellulosic fibers, or any combination thereof. For example, in one embodiment, the additive composition may comprise a thermoplastic polymer combined with a lotion, a thermoplastic polymer combined with a debonder, or a thermoplastic polymer combined with a softener.

In still another embodiment, the additive composition may comprise an adhesive, such as a latex polymer. The adhesive or latex polymer may be combined with any of the above described additives. Examples of adhesives that may be used include, for instance, vinyl acetates, ethylene carbon monoxide copolymers, polyacrylates, and natural and synthetic rubber materials, such as styrene butadiene rubbers. In still another embodiment, the adhesive may comprise a starch, such as a starch blend.

Any of the above described additive compositions can also be combined with various other ingredients. For instance, in one embodiment, the additive composition may contain in minor amounts of aloe and/or vitamin E that are intended to transfer to the base sheet from the creping surface.

As described above, in one embodiment, the additive composition may comprise a thermoplastic resin. The thermoplastic resin may be contained, for instance, in an aqueous dispersion prior to application to the creping surface. In one particular embodiment, the additive composition may comprise a non-fibrous olefin polymer. The additive composition, for instance, may comprise a film-forming composition and the olefin polymer may comprise an interpolymer of ethylene and at least one comonomer comprising an alkene, such as 1-octene. The additive composition may also contain a dispersing agent, such as a carboxylic acid. Examples of particular dispersing agents, for instance, include fatty acids, such as oleic acid or stearic acid.

In one particular embodiment, the additive composition may contain an ethylene and octene copolymer in combination with an ethylene-acrylic acid copolymer. The ethylene-acrylic acid copolymer is not only a thermoplastic resin, but may also serve as a dispersing agent. The ethylene and octene copolymer may be present in combination with the ethylene-acrylic acid copolymer in a weight ratio of from about 1:10 to about 10:1, such as from about 2:3 to about 3:2.

The olefin polymer composition may exhibit a crystallinity of less than about 50%, such as less than about 20%. The olefin polymer may also have a melt index of less than about 1000 g/10 min, such as less than about 700 g/10 min. The olefin polymer may also have a relatively small particle size, such as from about 0.1 micron to about 5 microns when contained in an aqueous dispersion.

In an alternative embodiment, the additive composition may contain an ethylene-acrylic acid copolymer. The ethylene-acrylic acid copolymer may be present in the above additive composition in combination with a dispersing agent, such as a fatty acid.

Once applied to a tissue web, it has been discovered that the additive composition may form a discontinuous but interconnected film depending upon the amount applied to the web. In other embodiments, the additive composition may be applied to a web such that the additive composition forms discrete treated areas on the surface of the web.

When containing a thermoplastic resin as described above, the additive composition may improve various properties of the base sheet. For instance, the additive composition provides the base sheet with a lotiony and soft feel. One test that measures one aspect of softness is called the Stick-Slip Test. During the Stick-Slip Test, a sled is pulled over a surface of the base sheet while the resistive force is measured. A higher Stick-Slip number indicates a more lotiony surface with lower drag forces. Tissue webs treated in accordance with the present disclosure, for instance, can have a Stick-Slip on one side of greater than about −0.01, such as from about −0.006 to about 0.7, such as from about 0 to about 0.7.

In addition, the additive composition when containing the thermoplastic resin may also increase the strength of the product while also enhancing softness.

The base sheets treated in accordance with the present disclosure can be made entirely from cellulosic fibers, such as pulp fibers, can be made from other natural fibers, can be made from synthetic fibers, or can be made from a mixture of different fibers. For instance, the base sheets can comprise cellulosic fibers in combination with synthetic fibers.

Base sheets that may be treated in accordance with the present disclosure include wet-laid tissue webs. The sheet-like products made in accordance with the present disclosure, for instance, may comprise bath tissue, facial tissue, paper towels, industrial wipers, premoistened wipers, and the like. The product may contain one-ply or may contain multiple plies.

In other embodiments, however, the base sheet may comprise an airlaid web, a hydroentangled web, a coform web, a spunbond web, a meltblown web, and the like. In still other embodiments, the base sheet may comprise a woven material or a knitted material.

Other features and aspects of the present disclosure are discussed in greater detail below.

BRIEF DESCRIPTION OF THE DRAWINGS

A full and enabling disclosure of the present invention, including the best mode thereof to one of ordinary skill in the art, is set forth more particularly in the remainder of the specification, including reference to the accompanying figures in which.

Figure 1:
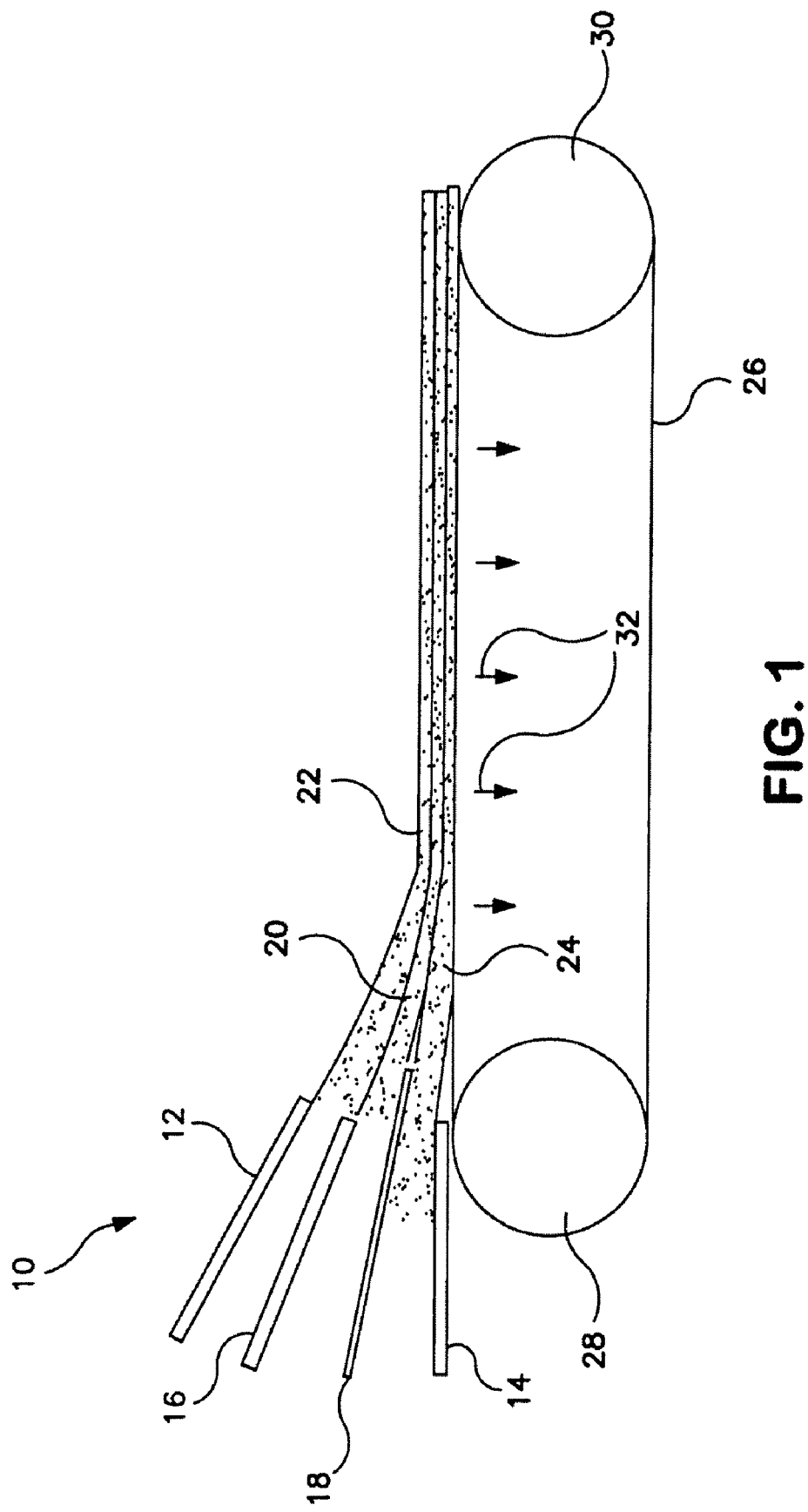
FIG. 1 is a schematic diagram of a tissue web forming machine, illustrating the formation of a stratified tissue web having multiple layers in accordance with the present disclosure.

Repeat use of reference characters in the present specification and drawings is intended to represent same or analogous features or elements of the present disclosure.

DETAILED DESCRIPTION

It is to be understood by one of ordinary skill in the art that the present discussion is a description of exemplary embodiments only, and is not intended as limiting the broader aspects of the present disclosure.

In general, the present disclosure is directed to the incorporation of an additive composition into a sheet-like product, such as a tissue web. More particularly, the present disclosure is directed to applying an additive composition to a creping surface. The additive composition adheres a base sheet to the creping surface for creping the base sheet from the surface. In addition to adhering the base sheet to the creping surface, the additive composition also transfers to the base sheet in amounts sufficient to increase the basis weight, such as more than 1% by weight. In this manner, sufficient amounts of the additive composition can be transferred to a sheet in order to improve one or more properties of the base sheet. In addition, during the process, the base sheet can be creped which may also increase the softness and bulk of the base sheet.

The additive composition may contain various ingredients and components. For example, in one embodiment, the additive composition may comprise a lotion that improves the feel of the base sheet and/or may be available for transfer to a user's skin for moisturizing the skin and providing other benefits. In general, any suitable lotion composition may be used in accordance with the present disclosure as long as the lotion is capable of adhering the base sheet to a creping surface.

In an alternative embodiment, the additive composition may comprise a thermoplastic polymer, such as an aqueous dispersion containing a thermoplastic resin. Once transferred to the base sheet, the thermoplastic resin may be configured to increase the strength of the base sheet, to improve the feel of the base sheet, and/or to enhance various other properties of the base sheet.

In addition to a lotion and a thermoplastic polymer dispersion, the additive composition may contain various other ingredients. For instance, other ingredients that may be contained within the additive composition include an adhesive, a latex polymer, a wax, an oxidized polyethylene, a polyurethane, a starch, a debonder, a softener, and/or various other beneficial agents, such as aloe or vitamin E. For instance, in one embodiment, the additive composition may comprise a lotion and/or thermoplastic polymer dispersion that contains various other ingredients that are added to provide some type of benefit either to the product or to the user of the product. In still another embodiment, a lotion may be combined with a thermoplastic polymer dispersion to form the additive composition of the present disclosure.

The base sheet that may be processed according to the present disclosure can vary depending upon the particular application and the desired result. The base sheet may comprise, for instance, a tissue web containing cellulosic fibers. In alternative embodiments, the base sheet may comprise nonwoven webs containing cellulosic fibers and synthetic fibers such as hydroentangled webs and coform webs. In other embodiments, nonwoven webs, such as meltblown webs and spunbond webs may still be used. In still other embodiments, woven materials and knitted materials may also be used in the process as long as the materials are capable of being adhered to a creping surface and removed.

In one particular embodiment, for instance, the process of the present disclosure is directed to forming wet pressed tissue webs. In this embodiment, an aqueous suspension of paper making fibers is formed into a tissue web which is then adhered to a creping surface while wet. For example, referring to FIG. 2 one embodiment of a process for forming wet pressed creped tissue webs is shown. In this embodiment, a headbox 60 emits an aqueous suspension of fibers onto a forming fabric 62 which is supported and driven by a plurality of guide rolls 64. A vacuum box 66 is disposed beneath forming fabric 62 and is adapted to remove water from the fiber furnish to assist in forming a web. From forming fabric 62, a formed web 68 is transferred to a second fabric 70, which may be either a wire or a felt. Fabric 70 is supported for movement around a continuous path by a plurality of guide rolls 72. Also included is a pick up roll 74 designed to facilitate transfer of web 68 from fabric 62 to fabric 70.

From fabric 70, web 68, in this embodiment, is transferred to the surface of a rotatable heated dryer drum 76, such as a Yankee dryer.

In accordance with the present disclosure, the additive composition can be incorporated into the tissue web 68 by being applied to the surface of the dryer drum 76 for transfer onto one side of the tissue web 68. In this manner, the additive composition is used to adhere the tissue web 68 to the dryer drum 76. In this embodiment, as web 68 is carried through a portion of the rotational path of the dryer surface, heat is imparted to the web causing most of the moisture contained within the web to be evaporated. Web 68 is then removed from dryer drum 76 by a creping blade 78. Creping web 78 as it is formed further reduces internal bonding within the web and increases softness. Applying the additive composition to the web during creping, on the other hand, may improve other properties of the web.

Figure 2:
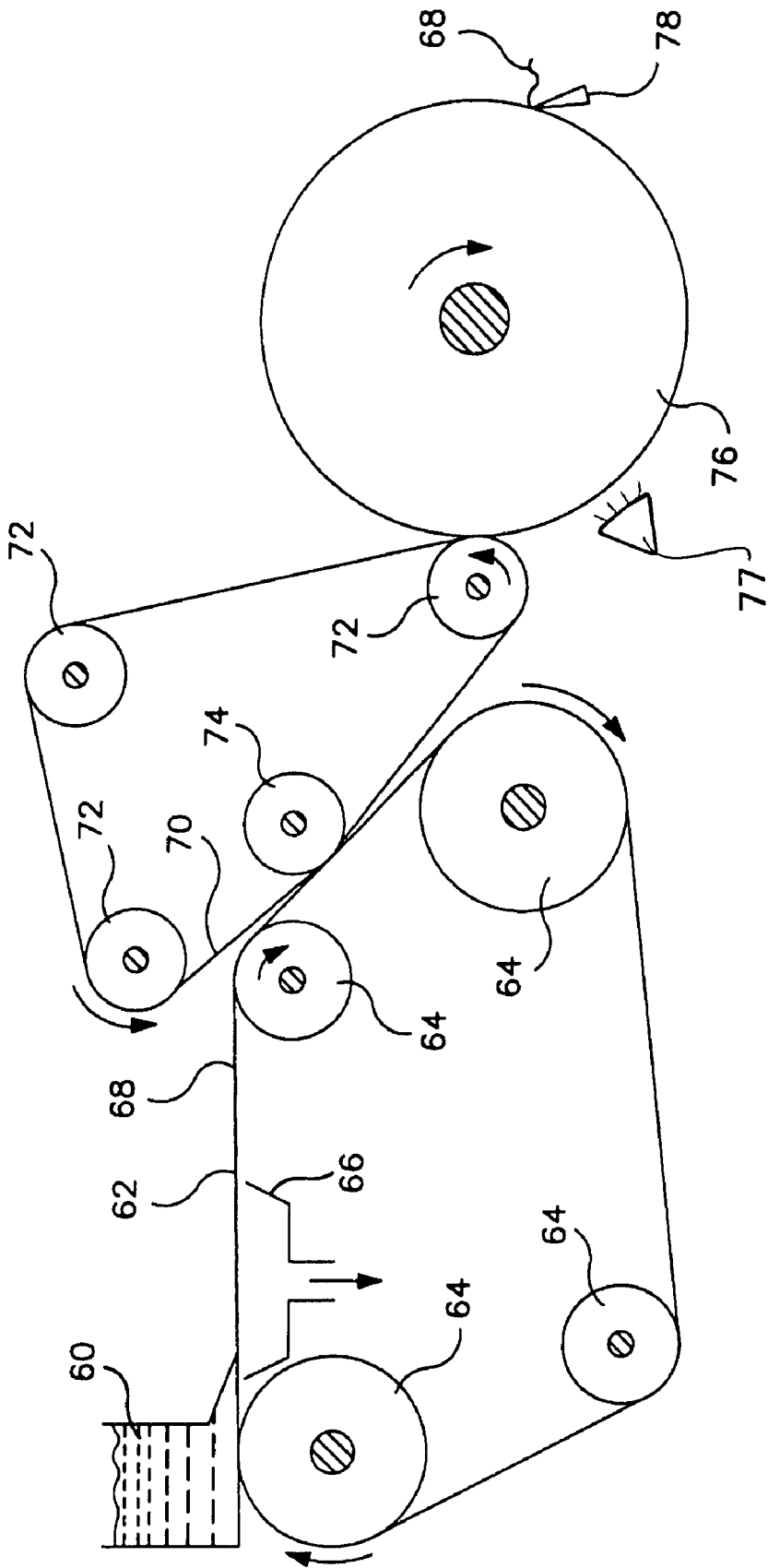
FIG. 2 is a schematic diagram of one embodiment of a process for forming wet pressed, creped tissue webs for use in the present disclosure.

The additive composition can be applied to the creping surface using any suitable technique. For instance, as shown in FIG. 2, in one embodiment, the additive composition can be sprayed onto the creping surface. In other embodiments, however, the additive composition can be printed onto the surface, extruded onto the surface, or applied using any suitable technique.

In accordance with the present disclosure, substantial amounts of the additive composition are transferred to the tissue web during the creping process. For instance, the basis weight of the web may increase by more than 1% by weight due to the amount of additive composition that is transferred. More particularly, the additive composition may be transferred to the web in an amount from about 2% to about 50% by weight, such as from about 2% to about 40% by weight, such as from about 2% to about 30% by weight. In various embodiments, for instance, the additive composition may transfer to the tissue web in an amount from about 5% to about 25% by weight, such as from an amount of about 5% to about 15% by weight.

As described, in one embodiment, the additive composition may comprise a thermoplastic polymer resin. The thermoplastic polymer resin may be applied to the creping surface in a form of an aqueous dispersion. Once transferred to the tissue web in accordance with the present disclosure, the polymer dispersion may improve various properties of the web. For instance, the polymer may improve the geometric means tensile strength and the geometric mean tensile energy absorbed of the web. Further, the strength of the web may be improved without adversely impacting the stiffness of the web. In fact, the thermoplastic polymer may improve the perceived softness of the web.

When comprising a thermoplastic resin, the additive composition generally contains an aqueous dispersion comprising at least one thermoplastic resin, water, and, optionally, at least one dispersing agent. The thermoplastic resin is present within the dispersion at a relatively small particle size. For example, the average volumetric particle size of the polymer may be less than about 5 microns. The actual particle size may depend upon various factors including the thermoplastic polymer that is present in the dispersion. Thus, the average volumetric particle size may be from about 0.05 microns to about 5 microns, such as less than about 4 microns, such as less than about 3 microns, such as less than about 2 microns, such as less than about 1 micron. Particle sizes can be measured on a Coulter LS230 light-scattering particle size analyzer or other suitable device. When present in the aqueous dispersion and when present in the tissue web, the thermoplastic resin is typically found in a non-fibrous form.

The particle size distribution (polydispersity) of the polymer particles in the dispersion may be less than or equal to about 2.0, such as less than 1.9, 1.7 or 1.5.

Examples of aqueous dispersions that may be incorporated into the additive composition of the present disclosure are disclosed, for instance, in U.S. Patent Application Publication No. 2005/0100754, U.S. Patent Application Publication No. 2005/0192365, PCT Publication No. WO 2005/021638, and PCT Publication No. WO 2005/021622, which are all incorporated herein by reference.

In one embodiment, the additive composition may comprise a film forming composition capable of forming a film on the surface of a tissue web. For instance, when applied to a tissue web, the additive composition can form a discontinuous but interconnected film. In other words, the additive composition forms an interconnected polymer network over the surface of the tissue web. The film or polymer network, however, is discontinuous in that various openings are contained within the film. The size of the openings can vary depending upon the amount of additive composition that is applied to the web and the manner in which the additive composition is applied. Of particular advantage, the openings allow liquids to be absorbed through the discontinuous film and into the interior of the tissue web. In this regard, the wicking properties of the tissue web are not substantially affected by the presence of the additive composition.

In other embodiments, the additive composition does not form an interconnected network but, instead, appears on the base sheet as treated discrete areas.

In this embodiment, the additive composition can remain primarily on the surface of the tissue web. In this manner, not only does the discontinuous film allow the tissue web to absorb fluids that contact the surface but also does not significantly interfere with the ability of the tissue web to absorb relatively large amounts of fluid. Thus, the additive composition does not significantly interfere with the liquid absorption properties of the web while increasing the strength of the web without substantially impacting adversely on the stiffness of the web.

The thickness of the additive composition when present on the surface of a base sheet can vary depending upon the ingredients of the additive composition and the amount applied. In general, for instance, the thickness can vary from about 0.01 microns to about 10 microns. At higher add-on levels, for instance, the thickness may be from about 3 microns to about 8 microns. At lower add-on levels, however, the thickness may be from about 0.1 microns to about 1 micron, such as from about 0.3 microns to about 0.7 microns.

At relatively low add-on levels, the additive composition may also deposit differently on the base sheet than when at relatively high add-on levels. For example, at relatively low add-on levels, not only do discrete treated areas form on the base sheet, but the additive composition may better follow the topography of the base sheet. For instance, in one embodiment, it has been discovered that the additive composition follows the crepe pattern of a base sheet when the base sheet is creped.

The thermoplastic resin contained within the additive composition may vary depending upon the particular application and the desired result. In one embodiment, for instance, thermoplastic resin is an olefin polymer. As used herein, an olefin polymer refers to a class of unsaturated open-chain hydrocarbons having the general formula $C_nH_{2n}$. The olefin polymer may be present as a copolymer, such as an interpolymer. As used herein, a substantially olefin polymer refers to a polymer that contains less than about 1% substitution.

In one particular embodiment, for instance, the olefin polymer may comprise an alpha-olefin interpolymer of ethylene with at least one comonomer selected from the group consisting of a $C_4$-$C_{20}$ linear, branched or cyclic diene, or an ethylene vinyl compound, such as vinyl acetate, and a compound represented by the formula $H_2C$=CHR wherein R is a $C_1$-$C_{20}$ linear, branched or cyclic alkyl group or a $C_6$-$C_{20}$ aryl group. Examples of comonomers include propylene, 1-butene, 3-methyl-1-butene, 4-methyl-1-pentene, 3-methyl-1-pentene, 1-heptene, 1-hexene, 1-octene, 1-decene, and 1-dodecene. In some embodiments, the interpolymer of ethylene has a density of less than about 0.92 g/cc.

In other embodiments, the thermoplastic resin comprises an alpha-olefin interpolymer of propylene with at least one comonomer selected from the group consisting of ethylene, a $C_4$-$C_{20}$ linear, branched or cyclic diene, and a compound represented by the formula $H_2C$=CHR wherein R is a $C_1$-$C_{20}$ linear, branched or cyclic alkyl group or a $C_6$-$C_{20}$ aryl group. Examples of comonomers include ethylene, 1-butene, 3-methyl-1-butene, 4-methyl-1-pentene, 3-methyl-1-pentene, 1-heptene, 1-hexene, 1-octene, 1-decene, and 1-dodecene. In some embodiments, the comonomer is present at about 5% by weight to about 25% by weight of the interpolymer. In one embodiment, a propylene-ethylene interpolymer is used.

Other examples of thermoplastic resins which may be used in the present disclosure include homopolymers and copolymers (including elastomers) of an olefin such as ethylene, propylene, 1-butene, 3-methyl-1-butene, 4-methyl-1-pentene, 3-methyl-1-pentene, 1-heptene, 1-hexene, 1-octene, 1-decene, and 1-dodecene as typically represented by polyethylene, polypropylene, poly-1-butene, poly-3-methyl-1-butene, poly-3-methyl-1-pentene, poly-4-methyl-1-pentene, ethylene-propylene copolymer, ethylene-1-butene copolymer, and propylene-1-butene copolymer; copolymers (including elastomers) of an alpha-olefin with a conjugated or non-conjugated diene as typically represented by ethylene-butadiene copolymer and ethylene-ethylidene norbornene copolymer; and polyolefins (including elastomers) such as copolymers of two or more alpha-olefins with a conjugated or non-conjugated diene as typically represented by ethylene-propylene-butadiene copolymer, ethylene-propylene-dicyclopentadiene copolymer, ethylene-propylene-1,5-hexadiene copolymer, and ethylene-propylene-ethylidene norbornene copolymer; ethylene-vinyl compound copolymers such as ethylene-vinyl acetate copolymers with N-methylol functional comonomers, ethylene-vinyl alcohol copolymers with N-methylol functional comonomers, ethylene-vinyl chloride copolymer, ethylene acrylic acid or ethylene-(meth)acrylic acid copolymers, and ethylene-(meth)acrylate copolymer; styrenic copolymers (including elastomers) such as polystyrene, ABS, acrylonitrile-styrene copolymer, methylstyrene-styrene copolymer; and styrene block copolymers (including elastomers) such as styrene-butadiene copolymer and hydrate thereof, and styrene-isoprene-styrene triblock copolymer; polyvinyl compounds such as polyvinyl chloride, polyvinylidene chloride, vinyl chloride-vinylidene chloride copolymer, polymethyl acrylate, and polymethyl methacrylate; polyamides such as nylon 6, nylon 6,6, and nylon 12; thermoplastic polyesters such as polyethylene terephthalate and polybutylene terephthalate; polycarbonate, polyphenylene oxide, and the like. These resins may be used either alone or in combinations of two or more.

In particular embodiments, polyolefins such as polypropylene, polyethylene, and copolymers thereof and blends thereof, as well as ethylene-propylene-diene terpolymers are used. In some embodiments, the olefinic polymers include homogeneous polymers described in U.S. Pat. No. 3,645,992 by Elston; high density polyethylene (HDPE) as described in U.S. Pat. No. 4,076,698 to Anderson; heterogeneously branched linear low density polyethylene (LLDPE); heterogeneously branched ultra low linear density (ULDPE); homogeneously branched, linear ethylene/alpha-olefin copolymers; homogeneously branched, substantially linear ethylene/alpha-olefin polymers which can be prepared, for example, by a process disclosed in U.S. Pat. Nos. 5,272,236 and 5,278,272, the disclosure of which process is incorporated herein by reference; and high pressure, free radical polymerized ethylene polymers and copolymers such as low density polyethylene (LDPE). In still another embodiment of the present invention, the thermoplastic resin comprises an ethylene-carboxylic acid copolymer, such as ethylene-acrylic acid (EAA) and ethylene-methacrylic acid copolymers such as for example those available under the tradenames PRIMACOR™ from The Dow Chemical Company, NUCREL™ from DuPont, and ESCOR™ from ExxonMobil, and described in U.S. Pat. Nos. 4,599,392, 4,988,781, and 5,384,373, each of which is incorporated herein by reference in its entirety, and ethylene-vinyl acetate (EVA) copolymers. Polymer compositions described in U.S. Pat. Nos. 6,538,070, 6,566,446, 5,869,575, 6,448,341, 5,677,383, 6,316,549, 6,111,023, or 5,844,045, each of which is incorporated herein by reference in its entirety, are also suitable in some embodiments. Of course, blends of polymers can be used as well. In some embodiments, the blends include two different Ziegler-Natta polymers. In other embodiments, the blends can include blends of a Ziegler-Natta and a metallocene polymer. In still other embodiments, the thermoplastic resin used herein is a blend of two different metallocene polymers.

In one particular embodiment, the thermoplastic resin comprises an alpha-olefin interpolymer of ethylene with a comonomer comprising an alkene, such as 1-octene. The ethylene and octene copolymer may be present alone in the additive composition or in combination with another thermoplastic resin, such as ethylene-acrylic acid copolymer. Of particular advantage, the ethylene-acrylic acid copolymer not only is a thermoplastic resin, but also serves as a dispersing agent. For some embodiments, the additive composition should comprise a film-forming composition. It has been found that the ethylene-acrylic acid copolymer may assist in forming films, while the ethylene and octene copolymer lowers the stiffness. When present together, the weight ratio between the ethylene and octene copolymer and the ethylene-acrylic acid copolymer may be from about 1:10 to about 10:1, such as from about 3:2 to about 2:3.

The thermoplastic resin, such as the ethylene and octene copolymer, may have a crystallinity of less than about 50%, such as less than about 25%. The polymer may have been produced using a single site catalyst and may have a weight average molecular weight of from about 15,000 to about 5 million, such as from about 20,000 to about 1 million. The molecular weight distribution of the polymer may be from about 1.01 to about 40, such as from about 1.5 to about 20, such as from about 1.8 to about 10.

Depending upon the thermoplastic polymer, the melt index of the polymer may range from about 0.001 g/10 min to about 1,000 g/10 min, such as from about 0.5 g/10 min to about 800 g/10 min. For example, in one embodiment, the melt index of the thermoplastic resin may be from about 100 g/10 min to about 700 g/10 min.

The thermoplastic resin may also have a relatively low melting point. For instance, the melting point of the thermoplastic resin may be less than about 140° C., such as less than 130° C., such as less than 120° C. For instance, in one embodiment, the melting point may be less than about 90° C. The glass transition temperature of the thermoplastic resin may also be relatively low. For instance, the glass transition temperature may be less than about 50° C., such as less than about 40° C.

The one or more thermoplastic resins may be contained within the additive composition in an amount from about 1% by weight to about 96% by weight. For instance, the thermoplastic resin may be present in the aqueous dispersion in an amount from about 10% by weight to about 70% by weight, such as from about 20% to about 50% by weight.

In addition to at least one thermoplastic resin, the aqueous dispersion may also contain a dispersing agent. A dispersing agent is an agent that aids in the formation and/or the stabilization of the dispersion. One or more dispersing agents may be incorporated into the additive composition.

In general, any suitable dispersing agent can be used. In one embodiment, for instance, the dispersing agent comprises at least one carboxylic acid, a salt of at least one carboxylic acid, or carboxylic acid ester or salt of the carboxylic acid ester. Examples of carboxylic acids useful as a dispersant comprise fatty acids such as montanic acid, stearic acid, oleic acid, and the like. In some embodiments, the carboxylic acid, the salt of the carboxylic acid, or at least one carboxylic acid fragment of the carboxylic acid ester or at least one carboxylic acid fragment of the salt of the carboxylic acid ester has fewer than 25 carbon atoms. In other embodiments, the carboxylic acid, the salt of the carboxylic acid, or at least one carboxylic acid fragment of the carboxylic acid ester or at least one carboxylic acid fragment of the salt of the carboxylic acid ester has 12 to 25 carbon atoms. In some embodiments, carboxylic acids, salts of the carboxylic acid, at least one carboxylic acid fragment of the carboxylic acid ester or its salt has 15 to 25 carbon atoms are preferred. In other embodiments, the number of carbon atoms is 25 to 60. Some examples of salts comprise a cation selected from the group consisting of an alkali metal cation, alkaline earth metal cation, or ammonium or alkyl ammonium cation.

In still other embodiments, the dispersing agent is selected from the group consisting of ethylene-carboxylic acid polymers, and their salts, such as ethylene-acrylic acid copolymers or ethylene-methacrylic acid copolymers.

In other embodiments, the dispersing agent is selected from alkyl ether carboxylates, petroleum sulfonates, sulfonated polyoxyethylenated alcohol, sulfated or phosphated polyoxyethylenated alcohols, polymeric ethylene oxide/propylene oxide/ethylene oxide dispersing agents, primary and secondary alcohol ethoxylates, alkyl glycosides and alkyl glycerides.

When ethylene-acrylic acid copolymer is used as a dispersing agent, the copolymer may also serve as a thermoplastic resin.

In one particular embodiment, the aqueous dispersion contains an ethylene and octene copolymer, ethylene-acrylic acid copolymer, and a fatty acid, such as stearic acid or oleic acid. The dispersing agent, such as the carboxylic acid, may be present in the aqueous dispersion in an amount from about 0.1% to about 10% by weight.

In addition to the above components, the aqueous dispersion also contains water. Water may be added as tap water or as deionized water. The pH of the aqueous dispersion is generally less than about 12, such as from about 5 to about 11.5, such as from about 7 to about 11. The aqueous dispersion may have a solids content of less than about 75%, such as less than about 70%. For instance, the solids content of the aqueous dispersion may range from about 5% to about 60%.

While any method may be used to produce the aqueous dispersion, in one embodiment, the dispersion may be formed through a melt-kneading process. For example, the kneader may comprise a Banbury mixer, single-screw extruder or a multi-screw extruder. The melt-kneading may be conducted under the conditions which are typically used for melt-kneading the one or more thermoplastic resins.

In one particular embodiment, the process includes melt-kneading the components that make up the dispersion. The melt-kneading machine may include multiple inlets for the various components. For example, the extruder may include four inlets placed in series. Further, if desired, a vacuum vent may be added at an optional position of the extruder.

In some embodiments, the dispersion is first diluted to contain about 1 to about 3% by weight water and then, subsequently, further diluted to comprise greater than about 25% by weight water.

In an alternative embodiment, instead of using a thermoplastic polymer dispersion, the additive composition may comprise a lotion. The lotion, for instance, can be formulated to not only adhere the tissue web to the creping surface but may also be designed to transfer to the surface of the web in amounts sufficient to later provide benefits to the user. For instance, in one embodiment, the lotion can be transferred to the tissue web in an amount sufficient such that the lotion then later transfers to a user's skin when wiped across the skin by a user.

In general, any suitable lotion composition may be used that is capable of adhering the base sheet to the creping surface and thereafter transferring to the base sheet such that the base sheet increases in basis weight by greater than about 2% by weight. Examples of lotions that may be used in accordance with the present disclosure, for instance, are disclosed in U.S. Pat. No. 5,885,697, U.S. Patent Publication No. 2005/0058693, and/or U.S. Patent Publication No. 2005/0058833, which are all incorporated herein by reference.

In one embodiment, for instance, the lotion composition may comprise an oil, a wax, a fatty alcohol, and one or more other additional ingredients.

For instance, the amount of oil in the composition can be from about 30 to about 90 weight percent, more specifically from about 40 to about 70 weight percent, and still more specifically from about 45 to about 60 weight percent. Suitable oils include, but are not limited to, the following classes of oils: petroleum or mineral oils, such as mineral oil and petrolatum; animal oils, such as mink oil and lanolin oil; plant oils, such as aloe extract, sunflower oil and avocado oil; and silicone oils, such as dimethicone and alkyl methyl silicones.

The amount of wax in the composition can be from about 10 to about 40 weight percent, more specifically from about 10 to about 30 weight percent, and still more specifically from about 15 to about 25 weight percent. Suitable waxes include, but are not limited to the following classes: natural waxes, such as beeswax and carnauba wax; petroleum waxes, such as paraffin and ceresin wax; silicone waxes, such as alkyl methyl siloxanes; or synthetic waxes, such as synthetic beeswax and synthetic sperm wax.

The amount of fatty alcohol in the composition, if present, can be from about 5 to about 40 weight percent, more specifically from about 10 to about 30 weight percent, and still more specifically from about 15 to about 25 weight percent. Suitable fatty alcohols include alcohols having a carbon chain length of $C_{14}$-$C_{30}$, including cetyl alcohol, stearyl alcohol, behenyl alcohol, and dodecyl alcohol.

In order to better enhance the benefits to consumers, additional ingredients can be used. The classes of ingredients and their corresponding benefits include, without limitation, $C_{10}$ or greater fatty alcohols (lubricity, body, opacity); fatty esters (lubricity, feel modification); vitamins (topical medicinal benefits); dimethicone (skin protection); powders (lubricity, oil absorption, skin protection); preservatives and antioxidants (product integrity); ethoxylated fatty alcohols; (wettability, process aids); fragrance (consumer appeal); lanolin derivatives (skin moisturization), colorants, optical brighteners, sunscreens, alpha hydroxy acids, natural herbal extracts, and the like.

In one embodiment, the lotion composition can further contain a humectant. Humectants are typically cosmetic ingredients used to increase the water content of the top layers of the skin or mucous membrane, by helping control the moisture exchange between the product, the skin, and the atmosphere. Humectants may include primarily hydroscopic materials. Suitable humectants for inclusion in the moisturizing and lubrication compositions of the present disclosure include urocanic acid, N-Acetyl ethanolamine, aloe vera gel, arginine PCA, chitosan PCA, copper PCA, Corn glycerides, dimethyl imidazolidinone, fructose, glucamine, glucose, glucose glutamate, glucuronic acid, glutamic acid, glycereth-7, glycereth-12, glycereth-20, glycereth-26, glycerin, honey, hydrogenated honey, hydrogenated starch hydrolysates, hydrolyzed corn starch, lactamide MEA, lactic acid, lactose lysine PCA, mannitol, methyl gluceth-10, methyl gluceth-20, PCA, PEG-2 lactamide, PEG-10 propylene glycol, polyamino acids, polysaccharides, polyamino sugar condensate, potassium PCA, propylene glycol, propylene glycol citrate, saccharide hydrolysate, saccharide isomerate, sodium aspartate, sodium lactate, sodium PCA, sorbitol, TEA-lactate, TEA-PCA, Urea, Xylitol, and the like and mixtures thereof. Preferred humectants include polyols, glycerine, ethoxylated glycerine, polyethylene glycols, hydrogenated starch hydrolsates, propylene glycol, silicone glycol and pyrrolidone carboxylic acid.

In one embodiment, a lotion or one of the above ingredients contained in a lotion can be combined with a polymer dispersion as described above to produce an additive composition in accordance with the present disclosure having desired properties.

In still another embodiment, the additive composition may contain an adhesive, such as a latex polymer. The adhesive may be used alone if capable of transferring to the base sheet in sufficient amounts. Alternatively, the adhesive can be combined with various other components, such as a lotion or a thermoplastic resin as described above.

Latex emulsion polymers useful in accordance with this disclosure can comprise aqueous emulsion addition copolymerized unsaturated monomers, such as ethylenic monomers, polymerized in the presence of surfactants and initiators to produce emulsion-polymerized polymer particles. Unsaturated monomers contain carbon-to-carbon double bond unsaturation and generally include vinyl monomers, styrenic monomers, acrylic monomers, allylic monomers, acrylamide monomers, as well as carboxyl functional monomers. Vinyl monomers include vinyl esters such as vinyl acetate, vinyl propionate and similar vinyl lower alkyl esters, vinyl halides, vinyl aromatic hydrocarbons such as styrene and substituted styrenes, vinyl aliphatic monomers such as alpha olefins and conjugated dienes, and vinyl alkyl ethers such as methyl vinyl ether and similar vinyl lower alkyl ethers. Acrylic monomers include lower alkyl esters of acrylic or methacrylic acid having an alkyl ester chain from one to twelve carbon atoms as well as aromatic derivatives of acrylic and methacrylic acid. Useful acrylic monomers include, for instance, methyl, ethyl, butyl, and propyl acrylates and methacrylates, 2-ethyl hexyl acrylate and methacrylate, cyclohexyl, decyl, and isodecyl acrylates and methacrylates, and similar various acrylates and methacrylates.

In accordance with this disclosure, a carboxyl-functional latex emulsion polymer can contain copolymerized carboxyl-functional monomers such as acrylic and methacrylic acids, fumaric or maleic or similar unsaturated dicarboxylic acids, where the preferred carboxyl monomers are acrylic and methacrylic acid. The carboxyl-functional latex polymers comprise by weight from about 1% to about 50% copolymerized carboxyl monomers with the balance being other copolymerized ethylenic monomers. Preferred carboxyl-functional polymers include carboxylated vinyl acetate-ethylene terpolymer emulsions such as Airflex® 426 Emulsion, commercially available from Air Products Polymers, LP.

In other embodiments, the adhesive may comprise an ethylene carbon monoxide copolymer, a polyacrylate, or a polyurethane. In other embodiments, the adhesive may comprise a natural or synthetic rubber. For instance, the adhesive may comprise a styrene butadiene rubber, such as a carboxylic styrene butadiene rubber. In still another embodiment, the adhesive may comprise a starch, such as a starch blended with an aliphatic polyester.

In one embodiment, the adhesive is combined with other components to form the additive composition. For instance, the adhesive may be contained in the additive composition in an amount less than about 80% by weight, such as less than about 60% by weight, such as less than about 40% by weight, such as less than about 20% by weight, such as from about 2% by weight to about 30% by weight.

In addition, a lotion and/or a polymer dispersion may be combined with various other additives or ingredients. For instance, in one embodiment, a debonder may be present within the additive composition. A debonder is a chemical species that softens or weakens a tissue sheet by preventing the formation of hydrogen bonds.

Suitable debonding agents that may be used in the present disclosure include cationic debonding agents such as fatty dialkyl quaternary amine salts, mono fatty alkyl tertiary amine salts, primary amine salts, imidazoline quaternary salts, silicone quaternary salt and unsaturated fatty alkyl amine salts. Other suitable debonding agents are disclosed in U.S. Pat. No. 5,529,665 to Kaun which is incorporated herein by reference. In particular, Kaun discloses the use of cationic silicone compositions as debonding agents.

In one embodiment, the debonding agent used in the process of the present disclosure is an organic quaternary ammonium chloride and, particularly, a silicone-based amine salt of a quaternary ammonium chloride.

In one embodiment, the debonding agent can be PROSOFT® TQ1003, marketed by the Hercules Corporation. For example, one debonding agent that can be used is as follows:

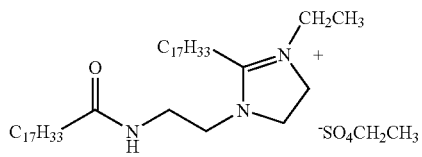

The chemical name for the above is:
1-Ethyl-2Noroleyl-3-Oleyl Amidoethyl Imidazolinium Ethosulfate.

In another embodiment, the additive composition may comprise a softener, such as a polysiloxane softener. Silicones, such as polysiloxanes, however, may interfere with the ability of the additive composition to adhere a base sheet to a creping surface. Thus, when present, the polysiloxane can be added to the additive composition in an amount of less than about 5% by weight.

Still in another embodiment, various beneficial agents can be incorporated into the additive composition in any amount as desired. For instance, in one embodiment, aloe, vitamin E, a wax, an oxidized polyethylene, or mixtures thereof can be combined into the additive composition in amounts less than about 5% by weight, such as from about 0.1% to about 3% by weight. Such ingredients can be combined into a lotion, into a polymer dispersion as described above, or into a mixture of both.

Once formulated, the additive composition can be applied to the creping surface, such as the surface of the Yankee dryer 76 as shown in FIG. 2 using any suitable method or technique. For instance, the additive composition can be sprayed onto the creping surface, extruded onto the creping surface, or printed onto the creping surface. When printed onto the creping surface using, for instance, a flexographic printer, the additive composition can be applied in a pattern. In other embodiments, a flooded nip may be used to apply the additive composition to the creping surface. In still other embodiments, the additive composition can be applied as a foam or can be applied according to a plasma coating process.

In one embodiment, the additive composition can be preheated prior to being applied to the creping surface. For example, in some embodiments, heating the additive composition may decrease the viscosity. In particular, in some embodiments, the additive composition may have a melting point of, for instance, from about 30° C. to about 70° C. If desired, the additive composition can be heated above the melting point and then applied to the creping surface.

As shown in FIG. 2 the creping surface comprises the surface of a Yankee dryer. In the embodiment illustrated in FIG. 2 the creping surface is heated in order to dry the tissue web as it is creped. For example, the creping surface can be heated to a temperature of from about 20° C. to about 150° C., such as from about 100° C. to about 130° C.

In the embodiment illustrated in FIG. 2 the tissue web is pressed against the creping surface while wet. For instance, the tissue web, in one embodiment, may have a consistency of from about 10% to about 30% solids, such as from about 10% to about 15% solids. In an alternative embodiment, however, the tissue web may be partially dried prior to being pressed against the creping surface. In this embodiment, for instance, the tissue web may have a consistency from about 30% to about 70% solids.

The amount of time that the base sheet stays in contact with the creping surface can depend upon numerous factors. For instance, the base sheet can stay in contact with the creping surface in an amount of time from as little as about 100 milliseconds to 10 seconds or even greater. A particular advantage, however, the additive composition is capable of both adhering to the base sheet and transferring to the base sheet in a very short amount of time. For instance, in one embodiment, the base sheet stays in contact with the creping surface in an amount of time from about 120 milliseconds to about 5 seconds, such as from about 120 milliseconds to about 2,000 milliseconds. In this embodiment, the base sheet can be moving at a speed of greater than about 1,000 feet per minute, such as from about 1,500 feet per minute to about 6,000 feet per minute or greater.

Figure 20:
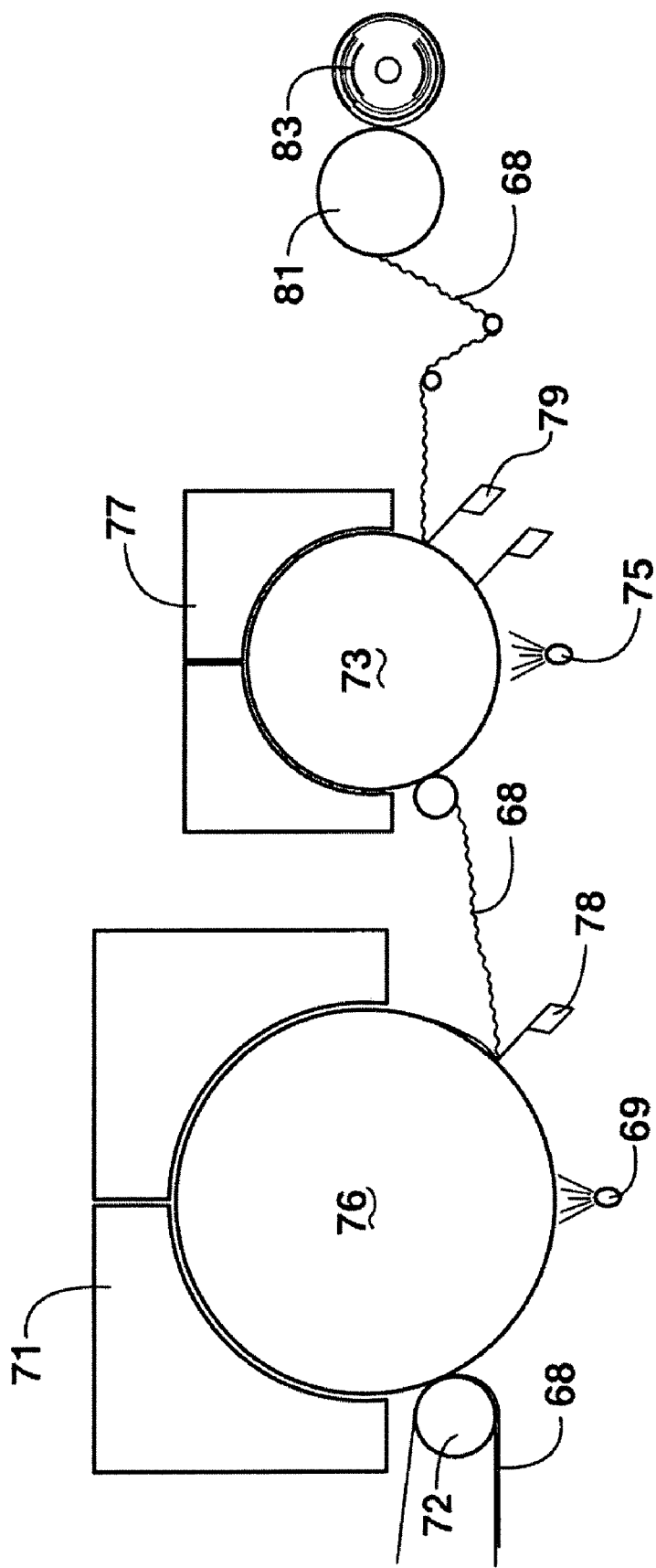
FIG. 20 is a schematic diagram of another embodiment of a process for forming creped tissue webs in accordance with the present disclosure.

Referring to FIG. 20 another alternative embodiment of a process for forming creped tissue webs is shown. Like reference numerals have been used to indicate similar elements with respect to the process illustrated in FIG. 2.

As shown in FIG. 20, the formed web 68 is transferred to the surface of the rotatable heated dryer drum 76, which may be a Yankee dryer. The press roll 72 may, in one embodiment, comprise a suction breast roll. In order to adhere the web 68 to the surface of the dryer drum 76, a creping adhesive may be applied to the surface of the dryer drum by a spraying device 69. The spraying device 69 may emit an additive composition made in accordance with the present disclosure or may emit a conventional creping adhesive.

As shown in FIG. 20, the web is adhered to the surface of the dryer drum 76 and then creped from the drum using the creping blade 78. If desired, the dryer drum 76 may be associated with a hood 71. The hood 71 may be used to force air against the web 68.

Once creped from the dryer drum 76, the web 68 is then adhered to a second dryer drum 73. The second dryer drum 73 may comprise, for instance, a heated drum surrounded by a hood 77. The drum may be heated to a temperature of from about 25° C. to about 200° C., such as from about 100° C. to about 150° C.

In order to adhere the web 68 to the second dryer drum 73, a second spray device 75 may emit an adhesive onto the surface of the dryer drum. In accordance with the present disclosure, for instance, the second spray device 75 may emit an additive composition as described above. The additive composition not only assists in adhering the tissue web 68 to the dryer drum 73, but also is transferred to the surface of the web as the web is creped from the dryer drum 73 by the creping blade 79.

Once creped from the second dryer drum 73, the web 68 may, optionally, be fed around a cooling reel drum 81 and cooled prior to being wound on a reel 83.

In the embodiment shown in FIG. 2 and in FIG. 20, the creping process is directly incorporated into the process for forming the web. These embodiments may be considered "in-line" processes. In an alternative embodiment, however, the base sheet may be formed and then subjected to the creping process.

Figure 21:
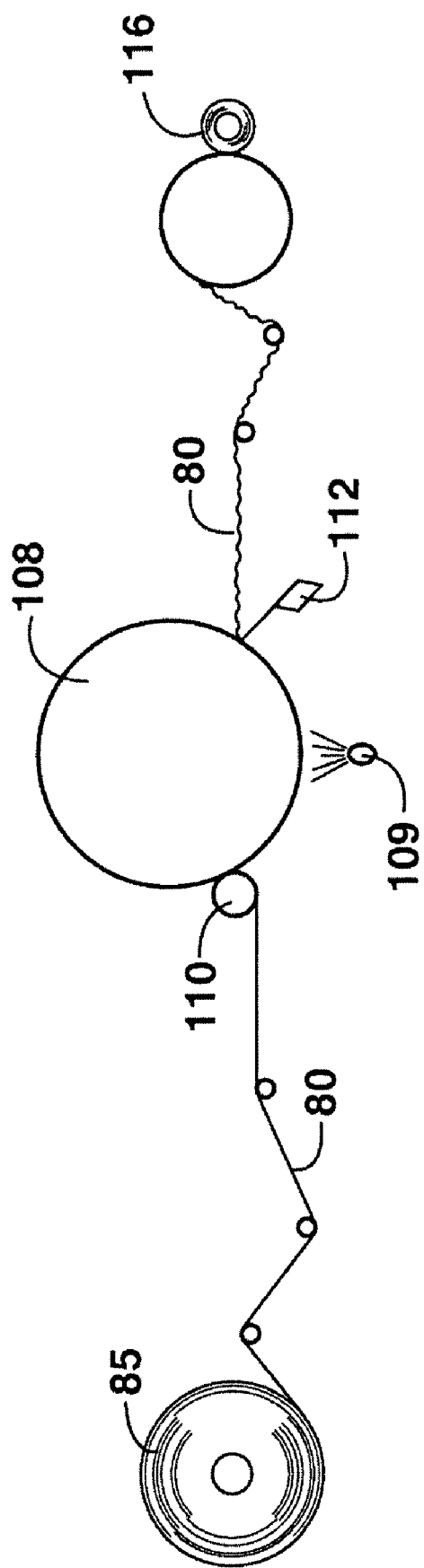
FIG. 21 is a schematic diagram of still another embodiment of a process for applying an additive composition to one side of a tissue web and creping one side of the web in accordance with the present disclosure.

For instance, referring to FIG. 21, still another embodiment of a process for applying the additive composition to one side of a base sheet in accordance with the present disclosure is illustrated. As shown, in this embodiment, a formed base sheet 80 is unwound from a roll 85 and fed into the process. This process may be considered an off-line process, although the application method may also be installed in-line.

As illustrated in FIG. 21, the base sheet 80 is pressed against a dryer drum 108 by a press roll 110. A spray device 109 applies the additive composition of the present disclosure to the surface of the dryer drum. The additive composition thus not only adheres the base sheet 80 to the surface of the dryer drum 108, but also transfers to the base sheet as the sheet is creped from the drum using a creping blade 112. Once creped from the dryer drum 108, the base sheet 80 is wound into a roll 116.

In the embodiment illustrated in FIG. 21, a preformed base sheet is creped from the rotating cylinder 108 when processing tissue webs, for instance, the tissue web is generally dry when adhered to the creping surface. For instance, the tissue web can have a consistency of greater than about 95%.

In the embodiment illustrated in FIG. 21, the creping surface may be at ambient temperature or may be heated. It should be understood, however, that it may not be necessary to heat the creping surface in the embodiment illustrated in FIG. 21 depending upon the additive composition that is used. In one embodiment, for instance, the additive composition itself may be preheated prior to being applied to the creping surface.

The amount of surface area that the additive composition covers on the base sheet when applied to the base sheet can vary. In general, for instance, the additive composition covers greater than about 10% of the surface are of one side of the base sheet. For instance, the additive composition may cover from about 20% to 100% of the surface are of the base sheet, such as from about 20% to about 90%, such as from about 20% to about 75%.

In the embodiments illustrated in the figures, only one side of the base sheet is treated with the additive composition. It should be understood, however, that both sides of the base sheet may be treated in accordance with the present disclosure. For instance, once one side of the base sheet is creped from a creping surface, the opposite side can be similarly adhered to a creping surface by the additive composition.

Numerous different types of base sheets may be processed according to the present disclosure. For instance, as particularly shown in FIGS. 2 and 20, in one embodiment, the base sheet comprises a tissue web containing cellulosic fibers.

Tissue products made according to the present disclosure may include single-ply tissue products or multiple-ply tissue products. For instance, in one embodiment, the product may include two plies or three plies.

In general, any suitable tissue web may be treated in accordance with the present disclosure. For example, in one embodiment, the base sheet can be a tissue product, such as a bath tissue, a facial tissue, a paper towel, an industrial wiper, and the like. Tissue products typically have a bulk of at least 3 cc/g. The tissue products can contain one or more plies and can be made from any suitable types of fiber.

Fibers suitable for making tissue webs comprise any natural or synthetic cellulosic fibers including, but not limited to nonwoody fibers, such as cotton, abaca, kenaf, sabai grass, flax, esparto grass, straw, jute hemp, bagasse, milkweed floss fibers, and pineapple leaf fibers; and woody or pulp fibers such as those obtained from deciduous and coniferous trees, including softwood fibers, such as northern and southern softwood kraft fibers; hardwood fibers, such as eucalyptus, maple, birch, and aspen. Pulp fibers can be prepared in high-yield or low-yield forms and can be pulped in any known method, including kraft, sulfite, high-yield pulping methods and other known pulping methods. Fibers prepared from organosolv pulping methods can also be used, including the fibers and methods disclosed in U.S. Pat. No. 4,793,898, issued Dec. 27, 1988 to Laamanen et al.; U.S. Pat. No. 4,594,130, issued Jun. 10, 1986 to Chang et al.; and U.S. Pat. No. 3,585,104. Useful fibers can also be produced by anthraquinone pulping, exemplified by U.S. Pat. No. 5,595,628 issued Jan. 21, 1997, to Gordon et al.

A portion of the fibers, such as up to 50% or less by dry weight, or from about 5% to about 30% by dry weight, can be synthetic fibers such as rayon, polyolefin fibers, polyester fibers, bicomponent sheath-core fibers, multi-component binder fibers, and the like. An exemplary polyethylene fiber is Fybrel®, available from Minifibers, Inc. (Jackson City, Tenn.). Any known bleaching method can be used. Synthetic cellulose fiber types include rayon in all its varieties and other fibers derived from viscose or chemically-modified cellulose. Chemically treated natural cellulosic fibers can be used such as mercerized pulps, chemically stiffened or crosslinked fibers, or sulfonated fibers. For good mechanical properties in using papermaking fibers, it can be desirable that the fibers be relatively undamaged and largely unrefined or only lightly refined. While recycled fibers can be used, virgin fibers are generally useful for their mechanical properties and lack of contaminants. Mercerized fibers, regenerated cellulosic fibers, cellulose produced by microbes, rayon, and other cellulosic material or cellulosic derivatives can be used. Suitable papermaking fibers can also include recycled fibers, virgin fibers, or mixes thereof. In certain embodiments capable of high bulk and good compressive properties, the fibers can have a Canadian Standard Freeness of at least 200, more specifically at least 300, more specifically still at least 400, and most specifically at least 500.

Other papermaking fibers that can be used in the present disclosure include paper broke or recycled fibers and high yield fibers. High yield pulp fibers are those papermaking fibers produced by pulping processes providing a yield of about 65% or greater, more specifically about 75% or greater, and still more specifically about 75% to about 95%. Yield is the resulting amount of processed fibers expressed as a percentage of the initial wood mass. Such pulping processes include bleached chemithermomechanical pulp (BCTMP), chemithermomechanical pulp (CTMP), pressure/pressure thermomechanical pulp (PTMP), thermomechanical pulp (TMP), thermomechanical chemical pulp (TMCP), high yield sulfite pulps, and high yield Kraft pulps, all of which leave the resulting fibers with high levels of lignin. High yield fibers are well known for their stiffness in both dry and wet states relative to typical chemically pulped fibers.

In general, any process capable of forming a base sheet can also be utilized in the present disclosure especially for webs processed according to FIG. 21. For example, a papermaking process of the present disclosure can utilize creping, wet creping, double creping, embossing, wet pressing, air pressing, through-air drying, creped through-air drying, uncreped through-air drying, hydroentangling, air laying, coform methods, as well as other steps known in the art.

Also suitable for products of the present disclosure are tissue sheets that are pattern densified or imprinted, such as the tissue sheets disclosed in any of the following U.S. Pat. Nos. 4,514,345 issued on Apr. 30, 1985, to Johnson et al.; 4,528,239 issued on Jul. 9, 1985, to Trokhan; 5,098,522 issued on Mar. 24, 1992; 5,260,171 issued on Nov. 9, 1993, to Smurkoski et al.; 5,275,700 issued on Jan. 4, 1994, to Trokhan; 5,328,565 issued on Jul. 12, 1994, to Rasch et al.; 5,334,289 issued on Aug. 2, 1994, to Trokhan et al.; 5,431,786 issued on Jul. 11, 1995, to Rasch et al.; 5,496,624 issued on Mar. 5, 1996, to Steltjes, Jr. et al.; 5,500,277 issued on Mar.

19, 1996, to Trokhan et al.; 5,514,523 issued on May 7, 1996, to Trokhan et al.; 5,554,467 issued on Sep. 10, 1996, to Trokhan et al.; 5,566,724 issued on Oct. 22, 1996, to Trokhan et al.; 5,624,790 issued on Apr. 29, 1997, to Trokhan et al.; and, 5,628,876 issued on May 13, 1997, to Ayers et al., the disclosures of which are incorporated herein by reference to the extent that they are non-contradictory herewith. Such imprinted tissue sheets may have a network of densified regions that have been imprinted against a drum dryer by an imprinting fabric, and regions that are relatively less densified (e.g., "domes" in the tissue sheet) corresponding to deflection conduits in the imprinting fabric, wherein the tissue sheet superposed over the deflection conduits was deflected by an air pressure differential across the deflection conduit to form a lower-density pillow-like region or dome in the tissue sheet.

If desired, various chemicals and ingredients may be incorporated into tissue webs that are processed according to the present disclosure. The following materials are included as examples of additional chemicals that may be applied to the web. The chemicals are included as examples and are not intended to limit the scope of the invention. Such chemicals may be added at any point in the papermaking process.

In general, the products of the present invention can be used in conjunction with any known materials and chemicals that are not antagonistic to its intended use. Examples of such materials include but are not limited to odor control agents, such as odor absorbents, activated carbon fibers and particles, baby powder, baking soda, chelating agents, zeolites, perfumes or other odor-masking agents, cyclodextrin compounds, oxidizers, and the like. Superabsorbent particles, synthetic fibers, or films may also be employed. Additional options include cationic dyes, optical brighteners, emollients, and the like.

The different chemicals and ingredients that may be incorporated into the base sheet may depend upon the end use of the product. For instance, various wet strength agents may be incorporated into the product. For bath tissue products, for example, temporary wet strength agents may be used. As used herein, wet strength agents are materials used to immobilize the bonds between fibers in the wet state. Typically, the means by which fibers are held together in paper and tissue products involve hydrogen bonds and sometimes combinations of hydrogen bonds and covalent and/or ionic bonds. In some applications, it may be useful to provide a material that will allow bonding to the fibers in such a way as to immobilize the fiber-to-fiber bond points and make them resistant to disruption in the wet state. The wet state typically means when the product is largely saturated with water or other aqueous solutions.

Any material that when added to a paper or tissue web results in providing the sheet with a mean wet geometric tensile strength:dry geometric tensile strength ratio in excess of 0.1 may be termed a wet strength agent.

Temporary wet strength agents, which are typically incorporated into bath tissues, are defined as those resins which, when incorporated into paper or tissue products, will provide a product which retains less than 50% of its original wet strength after exposure to water for a period of at least 5 minutes. Temporary wet strength agents are well known in the art. Examples of temporary wet strength agents include polymeric aldehyde-functional compounds such as glyoxylated polyacrylamide, such as a cationic glyoxylated polyacrylamide.

Such compounds include PAREZ 631 NC wet strength resin available from Lanxess of Trenton, N.J., and HERCO-BOND 1366, manufactured by Hercules, Inc. of Wilmington, Del. Another example of a glyoxylated polyacrylamide is PAREZ 745, which is a glyoxylated poly (acrylamide-co-diallyl dimethyl ammonium chloride).

For facial tissues and other tissue products, on the other hand, permanent wet strength agents may be incorporated into the base sheet. Permanent wet strength agents are also well known in the art and provide a product that will retain more than 50% of its original wet strength after exposure to water for a period of at least 5 minutes.

Once formed, the products may be packaged in different ways. For instance, in one embodiment, the sheet-like product may be cut into individual sheets and stacked prior to being placed into a package. Alternatively, the sheet-like product may be spirally wound. When spirally wound together, each individual sheet may be separated from an adjacent sheet by a line of weakness, such as a perforation line. Bath tissues and paper towels, for instance, are typically supplied to a consumer in a spirally wound configuration.

Tissue webs that may be treated in accordance with the present disclosure may include a single homogenous layer of fibers or may include a stratified or layered construction. For instance, the tissue web ply may include two or three layers of fibers. Each layer may have a different fiber composition. For example, referring to FIG. 1, one embodiment of a device for forming a multi-layered stratified pulp furnish is illustrated. As shown, a multi-layered headbox 10 generally includes an upper head box wall 12 and a lower head box wall 14. Headbox 10 further includes a first divider 16 and a second divider 18, which separate three fiber stock layers.

Each of the fiber layers comprise a dilute aqueous suspension of papermaking fibers. The particular fibers contained in each layer generally depends upon the product being formed and the desired results. For instance, the fiber composition of each layer may vary depending upon whether a bath tissue product, facial tissue product or paper towel is being produced. In one embodiment, for instance, middle layer 20 contains southern softwood kraft fibers either alone or in combination with other fibers such as high yield fibers. Outer layers 22 and 24, on the other hand, contain softwood fibers, such as northern softwood kraft.

In an alternative embodiment, the middle layer may contain softwood fibers for strength, while the outer layers may comprise hardwood fibers, such as eucalyptus fibers, for a perceived softness.

An endless traveling forming fabric 26, suitably supported and driven by rolls 28 and 30, receives the layered papermaking stock issuing from headbox 10. Once retained on fabric 26, the layered fiber suspension passes water through the fabric as shown by the arrows 32. Water removal is achieved by combinations of gravity, centrifugal force and vacuum suction depending on the forming configuration.

Forming multi-layered paper webs is also described and disclosed in U.S. Pat. No. 5,129,988 to Farrington, Jr., which is incorporated herein by reference.

The basis weight of tissue webs made in accordance with the present disclosure can vary depending upon the final product. For example, the process may be used to produce bath tissues, facial tissues, paper towels, industrial wipers, and the like. In general, the basis weight of the tissue products may vary from about 10 gsm to about 110 gsm, such as from about 20 gsm to about 90 gsm. For bath tissue and facial tissues, for instance, the basis weight may range from about 10 gsm to about 40 gsm. For paper towels, on the other hand, the basis weight may range from about 25 gsm to about 80 gsm.

The tissue web bulk may also vary from about 3 cc/g to 20 cc/g, such as from about 5 cc/g to 15 cc/g. The sheet "bulk" is calculated as the quotient of the caliper of a dry tissue sheet, expressed in microns, divided by the dry basis weight, expressed in grams per square meter. The resulting sheet bulk is expressed in cubic centimeters per gram. More specifically, the caliper is measured as the total thickness of a stack of ten representative sheets and dividing the total thickness of the stack by ten, where each sheet within the stack is placed with the same side up. Caliper is measured in accordance with TAPPI test method T411 om-89 "Thickness (caliper) of Paper, Paperboard, and Combined Board" with Note 3 for stacked sheets. The micrometer used for carrying out T411 om-89 is an Emveco 200-A Tissue Caliper Tester available from Emveco, Inc., Newberg, Oreg. The micrometer has a load of 2.00 kilo-Pascals (132 grams per square inch), a pressure foot area of 2500 square millimeters, a pressure foot diameter of 56.42 millimeters, a dwell time of 3 seconds and a lowering rate of 0.8 millimeters per second.

In multiple ply products, the basis weight of each tissue web present in the product can also vary. In general, the total basis weight of a multiple ply product will generally be the same as indicated above, such as from about 20 gsm to about 110 gsm. Thus, the basis weight of each ply can be from about 10 gsm to about 60 gsm, such as from about 20 gsm to about 40 gsm.

In one embodiment, tissue webs made according to the present disclosure can be incorporated into multiple-ply products. For instance, in one embodiment, a tissue web made according to the present disclosure can be attached to one or more other tissue webs for forming a wiping product having desired characteristics. The other webs laminated to the tissue web of the present disclosure can be, for instance, a wet-creped web, a calendered web, an embossed web, a through-air dried web, a creped through-air dried web, an uncreped through-air dried web, a hydroentangled web, a coform web, an airlaid web, and the like.

In one embodiment, when incorporating a tissue web made according to the present disclosure into a multiple-ply product, it may be desirable to only apply the additive composition to one side of the tissue web and to crepe the treated side of the web. The creped side of the web is then used to form an exterior surface of a multiple ply product. The untreated and uncreped side of the web, on the other hand, is attached by any suitable means to one or more plies.

In addition to wet lay processes as shown in FIG. 2, it should be understood that various other base sheets may be treated in accordance with the present disclosure. For instance, other base sheets that may be treated in accordance with the present disclosure include airlaid webs, coform webs, hydroentangled webs, meltblown webs, spunbond webs, woven materials, knitted materials, and the like. For instance, any of the above materials can be treated according to the process illustrated in FIG. 21.

Airlaid webs are formed in an air forming process in which a fibrous nonwoven layer is created. In the airlaying process, bundles of small fibers having typical lengths ranging from about 3 to about 52 millimeters (mm) are separated and entrained in an air supply and then deposited onto a forming screen, usually with the assistance of a vacuum supply. The randomly deposited fibers then are bonded to one another using, for example, hot air or a spray adhesive. The production of airlaid nonwoven composites is well defined in the literature and documented in the art. Examples include the DanWeb process as described in U.S. Pat. No. 4,640,810 to Laursen et al. and assigned to Scan Web of North America Inc, the Kroyer process as described in U.S. Pat. No. 4,494,278 to Kroyer et al. and U.S. Pat. No. 5,527,171 to Soerensen assigned to Niro Separation a/s, the method of U.S. Pat. No. 4,375,448 to Appel et al assigned to Kimberly-Clark Corporation, or other similar methods.

Other materials containing cellulosic fibers include coform webs and hydroentangled webs. In the coform process, at least one meltblown diehead is arranged near a chute through which other materials are added to a meltblown web while it is forming. Such other materials may be natural fibers, superabsorbent particles, natural polymer fibers (for example, rayon) and/or synthetic polymer fibers (for example, polypropylene or polyester), for example, where the fibers may be of staple length.

Coform processes are shown in commonly assigned U.S. Pat. Nos. 4,818,464 to Lau and 4,100,324 to Anderson et al., which are incorporated herein by reference. Webs produced by the coform process are generally referred to as coform materials. More particularly, one process for producing coform nonwoven webs involves extruding a molten polymeric material through a die head into fine streams and attenuating the streams by converging flows of high velocity, heated gas (usually air) supplied from nozzles to break the polymer streams into discontinuous microfibers of small diameter. The die head, for instance, can include at least one straight row of extrusion apertures. In general, the microfibers may have an average fiber diameter of up to about 10 microns. The average diameter of the microfibers can be generally greater than about 1 micron, such as from about 2 microns to about 5 microns. While the microfibers are predominantly discontinuous, they generally have a length exceeding that normally associated with staple fibers.

In order to combine the molten polymer fibers with another material, such as pulp fibers, a primary gas stream is merged with a secondary gas stream containing the individualized wood pulp fibers. Thus, the pulp fibers become integrated with the polymer fibers in a single step. The wood pulp fibers can have a length of from about 0.5 millimeters to about 10 millimeters. The integrated air stream is then directed onto a forming surface to air form the nonwoven fabric. The nonwoven fabric, if desired, may be passed into the nip of a pair of vacuum rolls in order to further integrate the two different materials.

Natural fibers that may be combined with the meltblown fibers include wool, cotton, flax, hemp and wood pulp. Wood pulps include standard softwood fluffing grade such as CR-1654 (US Alliance Pulp Mills, Coosa, Ala.). Pulp may be modified in order to enhance the inherent characteristics of the fibers and their processability. Curl may be imparted to the fibers by methods including chemical treatment or mechanical twisting. Curl is typically imparted before crosslinking or stiffening. Pulps may be stiffened by the use of crosslinking agents such as formaldehyde or its derivatives, glutaraldehyde, epichlorohydrin, methylolated compounds such as urea or urea derivatives, dialdehydes such as maleic anhydride, non-methylolated urea derivatives, citric acid or other polycarboxylic acids. Pulp may also be stiffened by the use of heat or caustic treatments such as mercerization. Examples of these types of fibers include NHB416 which is a chemically crosslinked southern softwood pulp fibers which enhances wet modulus, available from the Weyerhaeuser Corporation of Tacoma, Wash. Other useful pulps are debonded pulp (NF405) and non-debonded pulp (NB416) also from Weyerhaeuser. HPZ3 from Buckeye Technologies, Inc of Memphis, Tenn., has a chemical treatment that sets in a curl and twist, in addition to imparting added dry and wet stiffness and resilience to the fiber. Another suitable pulp is Buckeye HP2 pulp and still another is IP Supersoft from International Paper Corporation. Suitable rayon fibers are 1.5 denier Merge 18453 fibers from Acordis Cellulose Fibers Incorporated of Axis, Ala.

When containing cellulosic materials such as pulp fibers, a coform material may contain the cellulosic material in an amount from about 10% by weight to about 80% by weight, such as from about 30% by weight to about 70% by weight. For example, in one embodiment, a coform material may be produced containing pulp fibers in an amount from about 40% by weight to about 60% by weight.

In addition to coform webs, hydroentangled webs can also contain synthetic and pulp fibers. Hydroentangled webs refer to webs that have been subjected to columnar jets of a fluid that cause the fibers in the web to entangle. Hydroentangling a web typically increases the strength of the web. In one embodiment, pulp fibers can be hydroentangled into a continuous filament material, such as a spunbond web. The hydroentangled resulting nonwoven composite may contain pulp fibers in an amount from about 50% to about 80% by weight, such as in an amount of about 70% by weight. Commercially available hydroentangled composite webs as described above are commercially available from the Kimberly-Clark Corporation under the name HYDROKNIT. Hydraulic entangling is described in, for example, U.S. Pat. No. 5,389,202 to Everhart, which is incorporated herein by reference.

In addition to base sheets containing cellulosic fibers, the present disclosure is also directed to applying additive compositions to base sheets made entirely from synthetic fibers. For instance, in one embodiment, the base sheet may comprise a nonwoven meltblown web.

Meltblown fibers are formed by extruding a molten thermoplastic material through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al. Generally speaking, meltblown fibers may be microfibers that may be continuous or discontinuous, are generally smaller than 10 microns in diameter, and are generally tacky when deposited onto a collecting surface.

In still another embodiment, the base sheet may comprise a nonwoven spunbond web. Spunbonded fibers are small diameter substantially continuous fibers that are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spun-bonded nonwoven webs is described and illustrated, for example, in U.S. Pat. Nos. 4,340,563 to Appel, et al. 3,692,618 to Dorschner, et al., 3,802,817 to Matsuki et al., 3,338,992 to Kinney, 3,341,394 to Kinney, 3,502,763 to Hartman, 3,502,538 to Levy, 3,542,615 to Dobo, et al., and 5,382,400 to Pike, et al. Spunbond fibers are generally not tacky when they are deposited onto a collecting surface. Spunbond fibers can sometimes have diameters less than about 40 microns, and are often between about 5 to about 20 microns.

In still another embodiment, the base sheet might comprise a laminate. For instance, the base sheet may comprise a spunbond/meltblown/spunbond laminate.

In addition to nonwoven materials, the base sheet may also comprise a woven fabric or a knitted fabric. In general, any suitable base sheet may be treated in accordance with the present disclosure that is capable of adhering to a creping surface and being removed from the creping surface.

The present disclosure may be better understood with reference to the following examples.

EXAMPLE 1

In this example, tissue webs were made generally according to the process illustrated in FIG. 2 and formed into two-ply products. In order to adhere the tissue web to a creping surface, which in this embodiment comprised a Yankee dryer, additive compositions made according to the present disclosure were sprayed onto the dryer prior to contacting the dryer with the web. The samples were then subjected to various standardized tests.

For purposes of comparison, samples were also produced using a standard PVOH/KYMENE crepe package.

The following process was used to produce the samples.

Initially, 80 pounds of air-dried softwood kraft (NSWK) pulp was placed into a pulper and disintegrated for 15 minutes at 4% consistency at 120 degrees F. Then, the NSWK pulp was refined for 15 minutes, transferred to a dump chest and subsequently diluted to approximately 3% consistency. (Note: Refining fibrillates fibers to increase their bonding potential). Then, the NSWK pulp was diluted to about 2% consistency and pumped to a machine chest, such that the machine chest contained 20 air-dried pounds of NSWK at about 0.2-0.3% consistency. The above softwood fibers were utilized as the inner strength layer in a 3-layer tissue structure.

Two kilograms KYMENE® 6500, available from Hercules, Incorporated, located in Wilmington, Del., U.S.A., per metric ton of wood fiber and two kilograms per metric ton of wood fiber PAREZ® 631 NC, available from LANXESS Corporation., located in Trenton, N.J., U.S.A., was added and allowed to mix with the pulp fibers for at least 10 minutes before pumping the pulp slurry through the headbox.

Forty pounds of air-dried Aracruz ECF, a eucalyptus hardwood Kraft (EHWK) pulp available from Aracruz, located in Rio de Janeiro, RJ, Brazil, was placed into a pulper and disintegrated for 30 minutes at about 4% consistency at 120 degrees Fahrenheit. The EHWK pulp was then transferred to a dump chest and subsequently diluted to about 2% consistency.

Next, the EHWK pulp slurry was diluted, divided into two equal amounts, and pumped at about 1% consistency into two separate machine chests, such that each machine chest contained 20 pounds of air-dried EHWK. This pulp slurry was subsequently diluted to about 0.1% consistency. The two EHWK pulp fibers represent the two outer layers of the 3-layered tissue structure.

Two kilograms KYMENE® 6500 per metric ton of wood fiber was added and allowed to mix with the hardwood pulp fibers for at least 10 minutes before pumping the pulp slurry through the headbox.

The pulp fibers from all three machine chests were pumped to the headbox at a consistency of about 0.1%. Pulp fibers from each machine chest were sent through separate manifolds in the headbox to create a 3-layered tissue structure. The fibers were deposited on a forming fabric. Water was subsequently removed by vacuum.

The wet sheet, about 10-20% consistency, was transferred to a press felt or press fabric where it was further dewatered. The sheet was then transferred to a Yankee dryer through a nip via a pressure roll. The consistency of the wet sheet after the pressure roll nip (post-pressure roll consistency or PPRC) was approximately 40%. The wet sheet adhered to the Yankee dryer due to an adhesive that is applied to the dryer surface. Spray booms situated underneath the Yankee dryer sprayed either an adhesive package, which is a mixture of polyvinyl alcohol/KYMENE® 6500/Rezosol 2008M, or an additive composition according to the present disclosure onto the dryer surface. Rezosol 2008M is available from Hercules, Incorporated, located in Wilmington, Del., U.S.A.

One batch of the typical adhesive package on the continuous handsheet former (CHF) typically consisted of 25 gallons of water, 500 mL of a 6% solids polyvinyl alcohol solution, 75 mL of a 12.5% solids KYMENE® 6500 solution, and 20 mL of a 7.5% solids Rezosol 2008M solution.

The additive compositions according to the present disclosure varied in solids content from 2.5% to 10%.

The sheet was dried to about 95% consistency as it traveled on the Yankee dryer and to the creping blade. The creping blade subsequently scraped the tissue sheet and small amounts of dryer coating off the Yankee dryer. The creped tissue base sheet was then wound onto a 3" core into soft rolls for converting. Two rolls of the creped tissue were then rewound and plied together so that both creped sides were on the outside of the 2-ply structure. Mechanical crimping on the edges of the structure held the plies together. The plied sheet was then slit on the edges to a standard width of approximately 8.5 inches and folded. Tissue samples were conditioned and tested.

In particular, the following tests were performed on the samples:

Tensile Strength, Geometric Mean Tensile Strength (GMT), and Geometric Mean Tensile Energy Absorbed (GMTEA):

The tensile test that was performed used tissue samples that were conditioned at 23° C.+/−1° C. and 50%+/−2% relative humidity for a minimum of 4 hours. The 2-ply samples were cut into 3 inch wide strips in the machine direction (MD) and cross-machine direction (CD) using a precision sample cutter model JDC 15M-10, available from Thwing-Albert Instruments, a business having offices located in Philadelphia, Pa., U.S.A.

The gauge length of the tensile frame was set to four inches. The tensile frame was an Alliance RT/1 frame run with TestWorks 4 software. The tensile frame and the software are available from MTS Systems Corporation, a business having offices located in Minneapolis, Minn., U.S.A.

A 3" strip was then placed in the jaws of the tensile frame and subjected to a strain applied at a rate of 25.4 cm per minute until the point of sample failure. The stress on the tissue strip is monitored as a function of the strain. The calculated outputs included the peak load (grams-force/3", measured in grams-force), the peak stretch (%, calculated by dividing the elongation of the sample by the original length of the sample and multiplying by 100%), the % stretch @ 500 grams-force, the tensile energy absorption (TEA) at break (grams-force*cm/cm$^2$, calculated by integrating or taking the area under the stress-strain curve up the point of failure where the load falls to 30% of its peak value), and the slope A (kilograms-force, measured as the slope of the stress-strain curve from 57-150 grams-force).

Each tissue code (minimum of five replicates) was tested in the machine direction (MD) and cross-machine direction (CD). Geometric means of the tensile strength and tensile energy absorption (TEA) were calculated as the square root of the product of the machine direction (MD) and the cross-machine direction (CD). This yielded an average value that is independent of testing direction. The samples that were used are shown below.

Elastic Modulus (Maximum Slope) and Geometric Mean Modulus (GMM) as Measures of Sheet Stiffness:

Elastic Modulus (Maximum Slope) E(kg$_f$) is the elastic modulus determined in the dry state and is expressed in units of kilograms of force. Tappi conditioned samples with a width of 3 inches are placed in tensile tester jaws with a gauge length (span between jaws) of 4 inches. The jaws move apart at a crosshead speed of 25.4 cm/min and the slope is taken as the least squares fit of the data between stress values of 57 grams of force and 150 grams of force. If the sample is too weak to sustain a stress of at least 200 grams of force without failure, an additional ply is repeatedly added until the multi-ply sample can withstand at least 200 grams of force without failure. The geometric mean modulus or geometric mean slope was calculated as the square root of the product of the machine direction (MD) and the cross direction (CD) elastic moduli (maximum slopes), yielding an average value that is independent of testing direction.

Wet/Dry Tensile Test (% in the Cross Machine Direction)

The dry tensile test is described in Example 1, with the gauge length (span between jaws) being 2 inches. Wet tensile strength was measured in the same manner as dry strength except that the samples were wetted prior to testing. Specifically, in order to wet the sample, a 3"×5" tray was filled with distilled or deionized water at a temperature of 23±2° C. The water is added to the tray to an approximate one cm depth.

A 3M "Scotch-Brite" general purpose scrubbing pad is then cut to dimensions of 2.5"×4". A piece of masking tape approximately 5" long is placed along one of the 4" edges of the pad. The masking tape is used to hold the scrubbing pad.

The scrubbing pad is then placed into the water with the taped end facing up. The pad remains in the water at all times until testing is completed. The sample to be tested is placed on blotter paper that conforms to TAPPI T205. The scrubbing pad is removed from the water bath and tapped lightly three times on a screen associated with the wetting pan. The scrubbing pad is then gently placed on the sample parallel to the width of the sample in the approximate center. The scrubbing pad is held in place for approximately one second. The sample is then immediately put into the tensile tester and tested.

To calculate the wet/dry tensile strength ratio, the wet tensile strength value was divided by the dry tensile strength value.

The additive compositions of the present disclosure that were applied to the samples and tested in this example are as follows.

In the table below, AFFINITY™ EG8200 plastomer is an alpha-olefin interpolymer comprising an ethylene and octene copolymer that was obtained from The Dow Chemical Company of Midland, Mich., U.S.A. PRIMACOR™ 5980i copolymer is an ethylene-acrylic acid copolymer also obtained from The Dow Chemical Company. The ethylene-acrylic acid copolymer can serve not only as a thermoplastic polymer but also as a dispersing agent. INDUSTRENE® 106 comprises oleic acid, which is marketed by Chemtura Corporation, Middlebury, Conn. PRIMACOR™ 5980i copolymer contains 20.5% by weight acrylic acid and has a melt flow rate of 13.75 g/10 min at 125° C. and 2.16 kg as measured by ASTM D1238. AFFINITY™ EG8200G plastomer has a density of 0.87 g/cc as measured by ASTM D792 and has a melt flow rate of 5 g/10 min at 190° C. and 2.16 kg as measured by ASTM D1238.

| Sample No. | Polymer (wt. ratios in parentheses) | Dispersing Agent | Dispersing Agent conc. (wt. %) | % Solids |
|---|---|---|---|---|
| 1 | AFFINITY ™ EG8200/PRIMACOR ™ 5980i (60/40) | PRIMACOR ™ 5980i/Industrene ® 106 | 40.0/6.0 | 2.5 |
| 2 | AFFINITY ™ EG8200/PRIMACOR ™ 5980i (60/40) | PRIMACOR ™ 5980i | 40.0 | 2.5 |
| 3 | AFFINITY ™ EG8200/PRIMACOR ™ 5980i (60/40) | PRIMACOR ™ 5980i/Industrene ® 106 | 40.0/6.0 | 5 |
| 4 | AFFINITY ™ EG8200/PRIMACOR ™ 5980i (60/40) | PRIMACOR ™ 5980i | 40.0 | 5 |
| 5 | AFFINITY ™ EG8200/PRIMACOR ™ 5980i (60/40) | PRIMACOR ™ 5980i/Industrene ® 106 | 40.0/6.0 | 10 |

| Sample No | Polymer Particle size (um) | Poly-dispersity | Solids (wt. %) | pH | Viscosity (cp) | Temp (o C.) | RPM | Spindle |
|---|---|---|---|---|---|---|---|---|
| 1 | 1.01 | 1.57 | 32.1 | 10.3 | 572 | 21.7 | 50 | RV3 |
| 2 | 0.71 | 2.12 | 40.0 | 11.3 | 448 | 22.1 | 50 | RV3 |
| 3 | 1.01 | 1.57 | 32.1 | 10.3 | 572 | 21.7 | 50 | RV3 |
| 4 | 0.71 | 2.12 | 40.0 | 11.3 | 448 | 22.1 | 50 | RV3 |
| 5 | 1.01 | 1.57 | 32.1 | 10.3 | 572 | 21.7 | 50 | RV3 |

DOWICIL™ 200 antimicrobial, which is a preservative with the active composition of 96% c is 1-(3-chloroallyl)-3,5,7-triaza-1-azoniaadamantane chloride (also known as Quaternium-15) obtained from The Dow Chemical Company, was also present in each of the additive compositions.

As shown above, the percent solids in solution for the different additive compositions was varied. Varying the solids content in solution also varies the amount of solids incorporated into the base web. For instance, at 2.5% solution solids, it is estimated that from about 35 kg/MT to about 60 kg/MT solids is incorporated into the tissue web. At 5% solution solids, it is estimated that from about 70 kg/MT to about 130 kg/MT solids is incorporated into the tissue web. At 10% solution solids, it is estimated that from about 140 kg/MT to about 260 kg/MT solids is incorporated into the tissue web.

Figure 3:
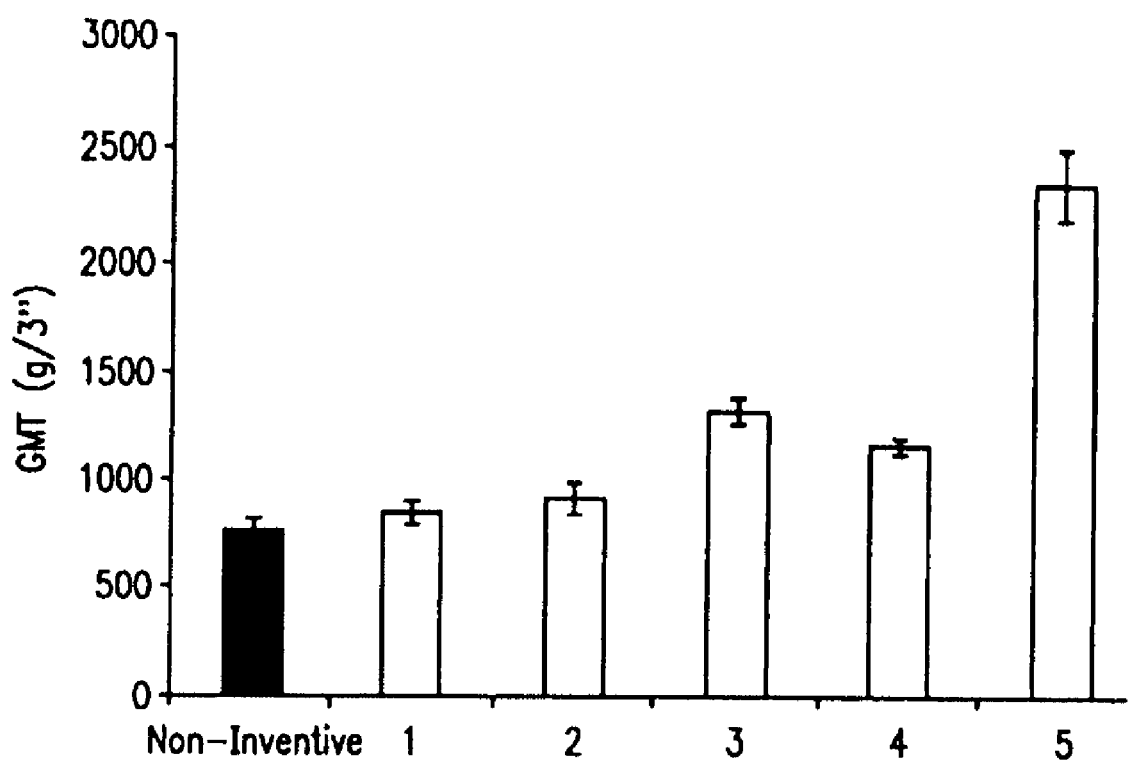
FIGS. 3-12 and 14-19 are the results obtained in the Examples as described below.
Figure 4:
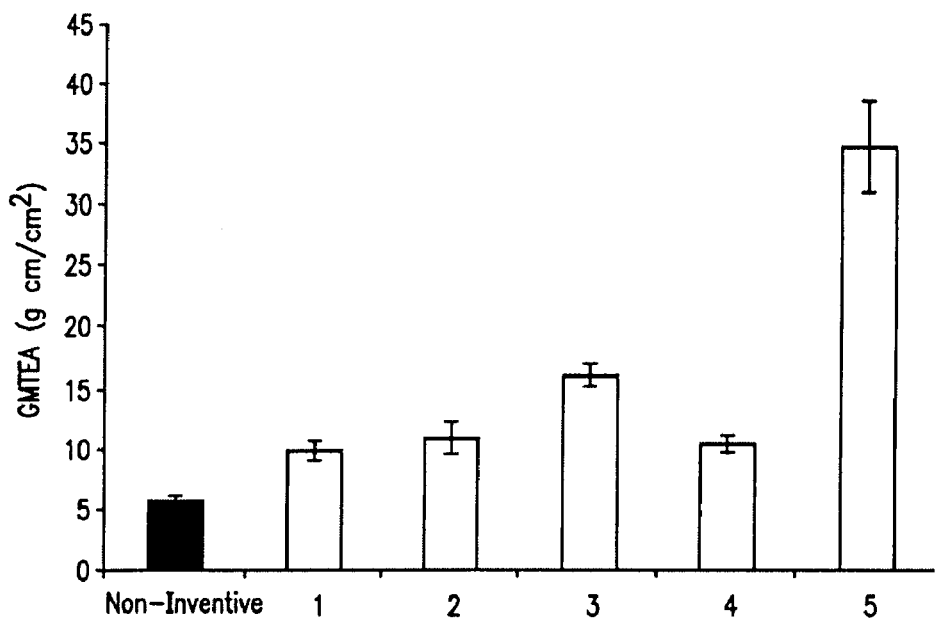
Figure 5:
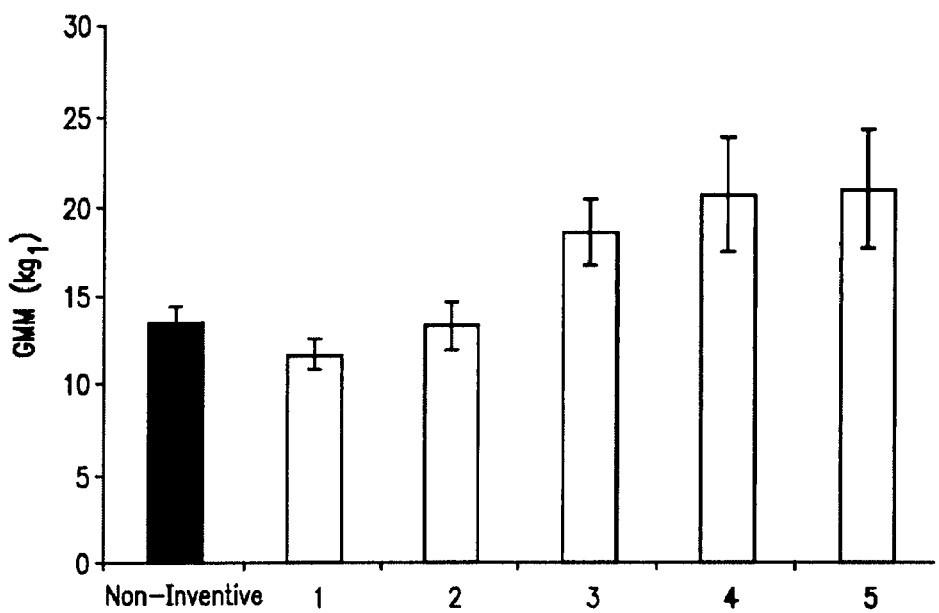
Figure 6:
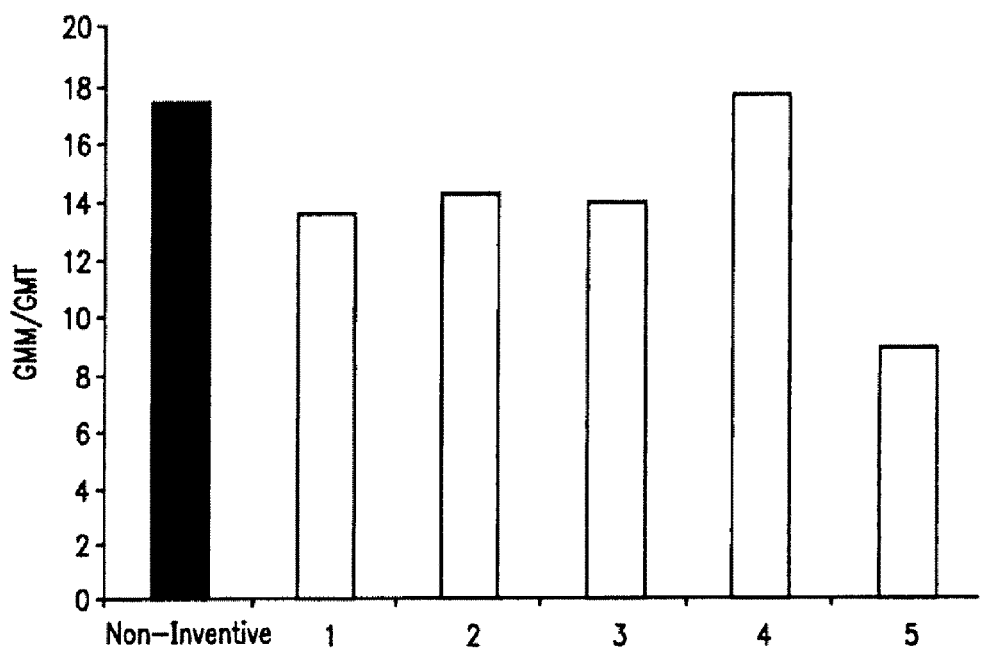
Figure 7:
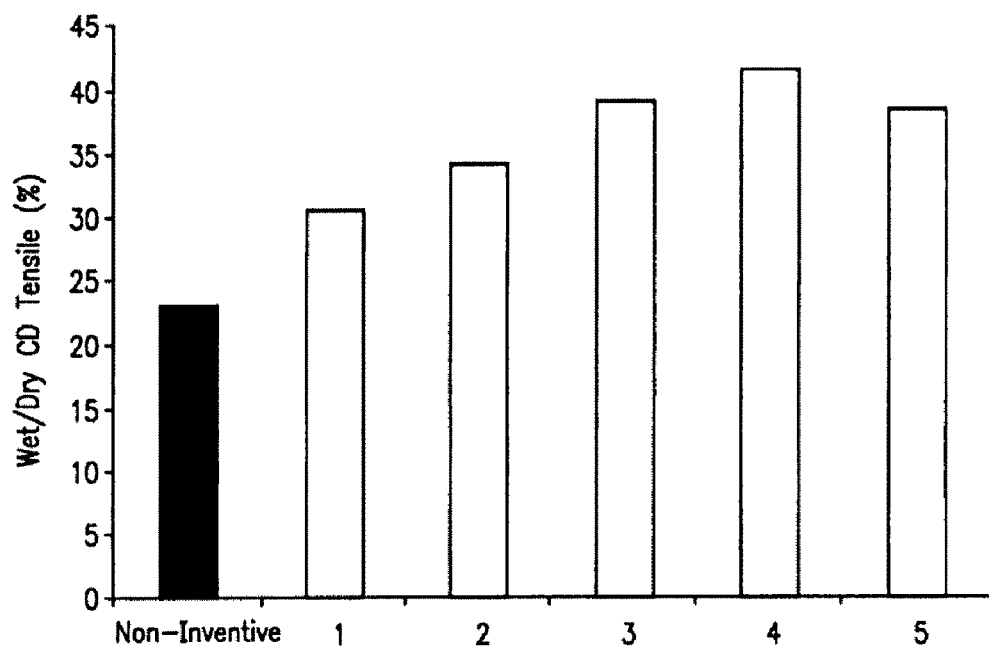

The results of this example are illustrated in FIGS. 3-7. As shown in FIG. 3, for instance, the geometric mean tensile strength of the samples made according to the present disclosure were greater than the non-inventive sample treated with the conventional bonding material. Similar results were also obtained for the geometric mean total energy absorbed.

Figure 8:
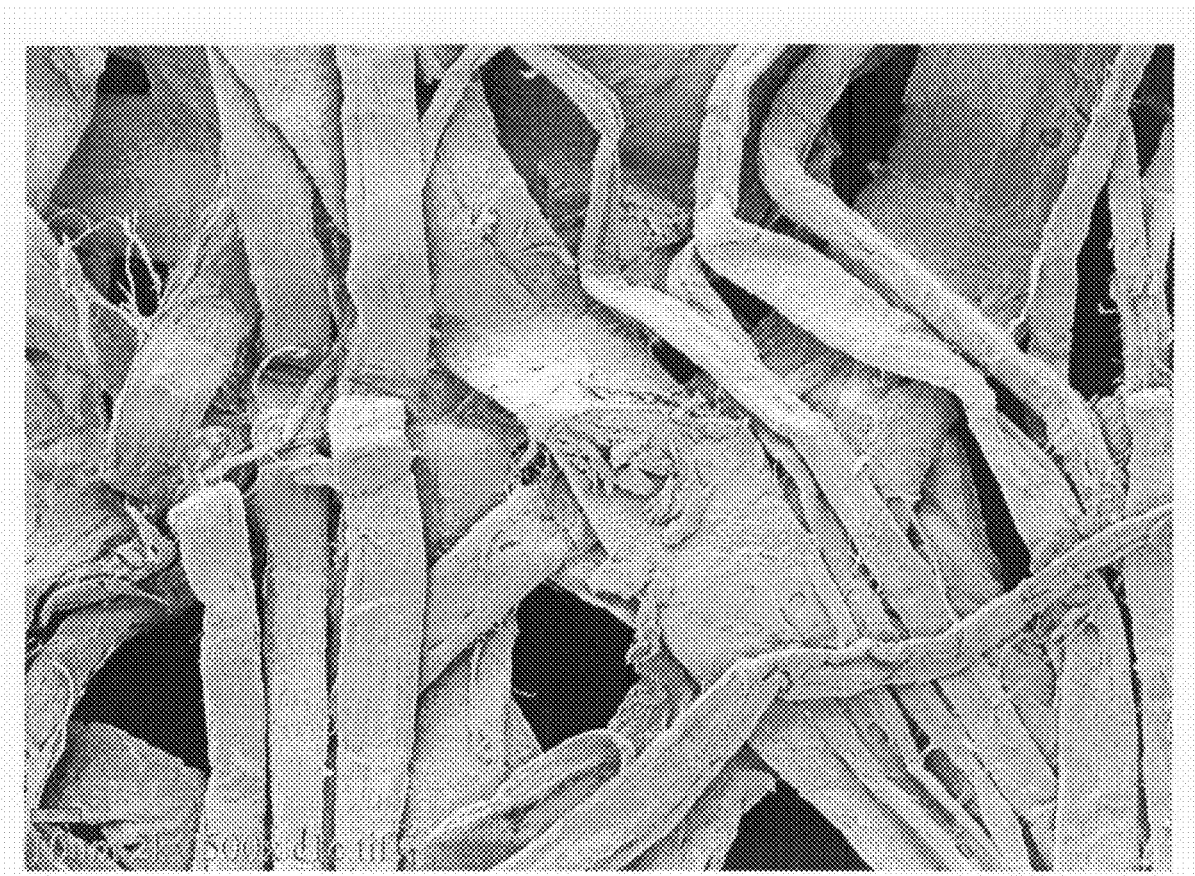
Figure 9:
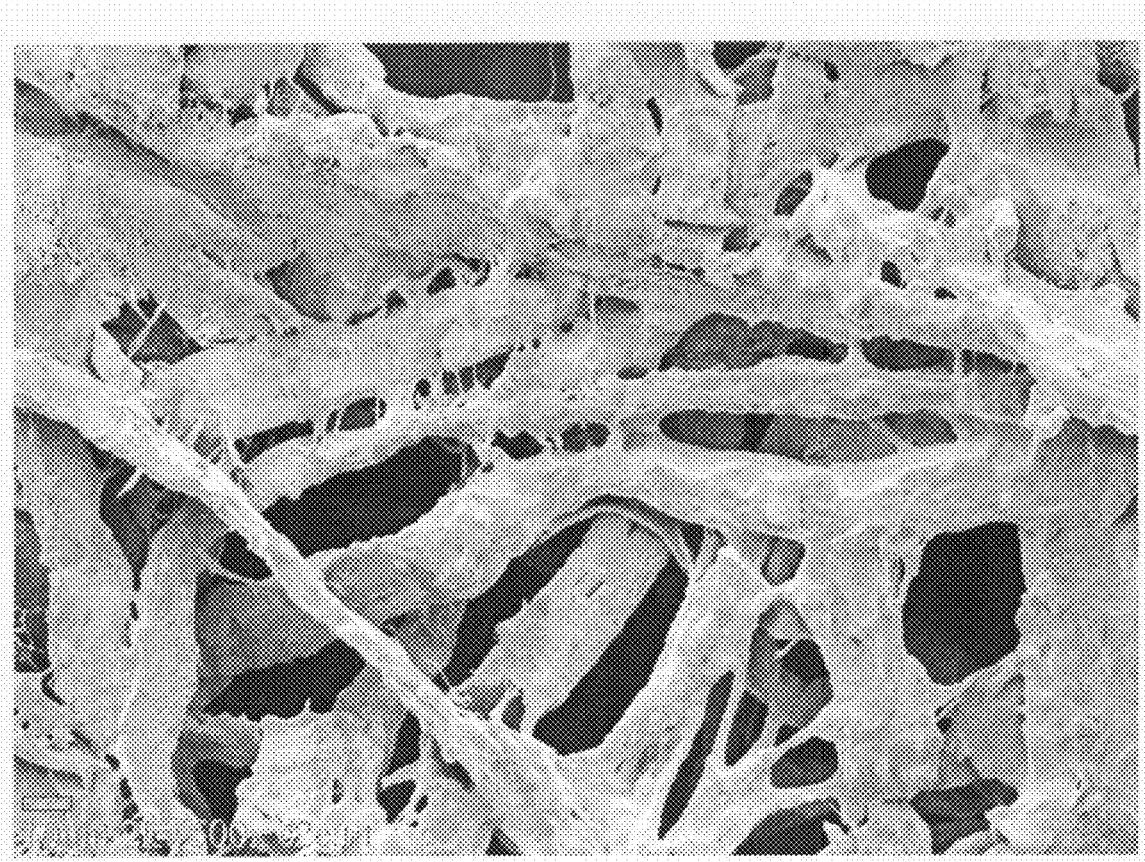
Figure 10:
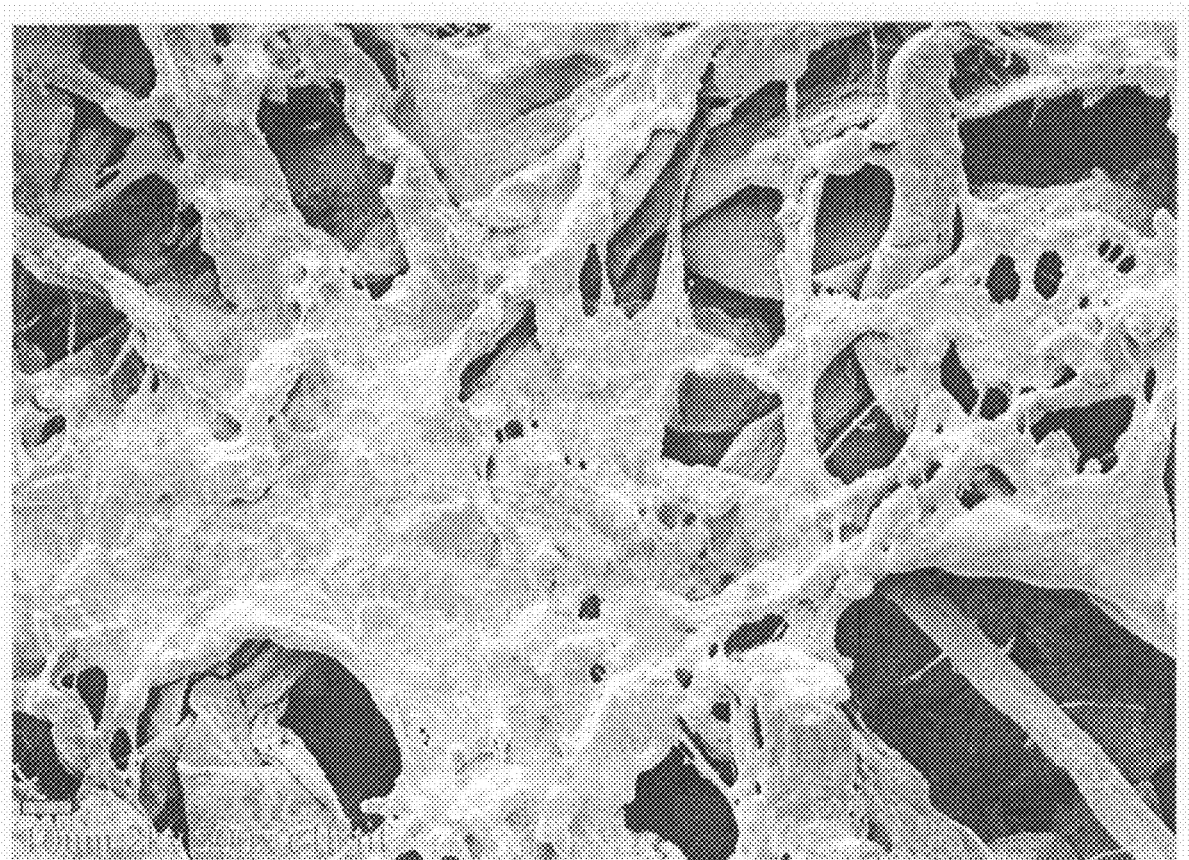
Figure 11:
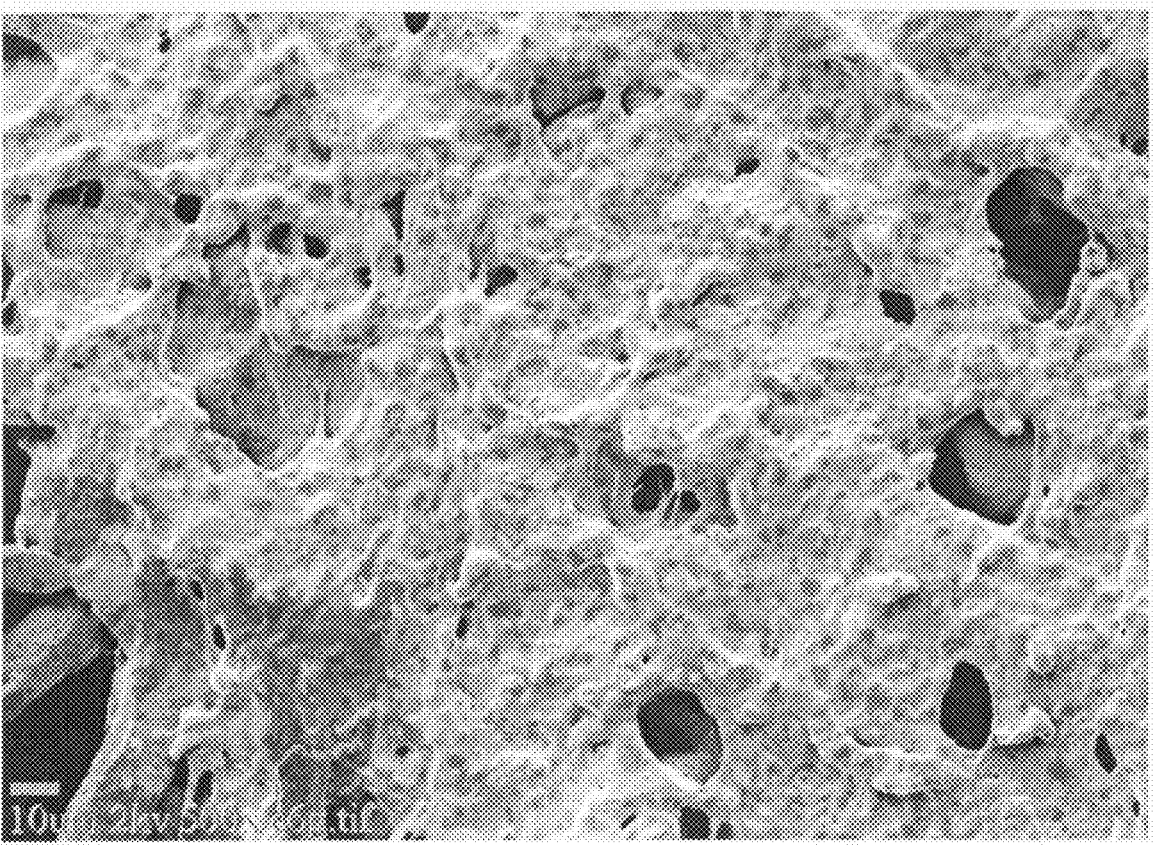

In addition to testing the properties of the samples, some of the samples were also photographed. For instance, referring to FIGS. 8, 9, 10 and 11, four of the samples are shown at 500 times magnification. In particular, FIG. 8 represents a photograph of the non-inventive sample, FIG. 9 is a photograph of Sample No. 1, FIG. 10 is a photograph of Sample No. 3, and FIG. 11 is a photograph of Sample No. 5. As shown, the additive composition of the present disclosure tends to form a discontinuous film over the surface of the tissue web. Further, the greater the solution solids, the greater the amount of film formation. These figures indicate that the additive composition generally remains on the surface of the tissue web.

Figure 12:
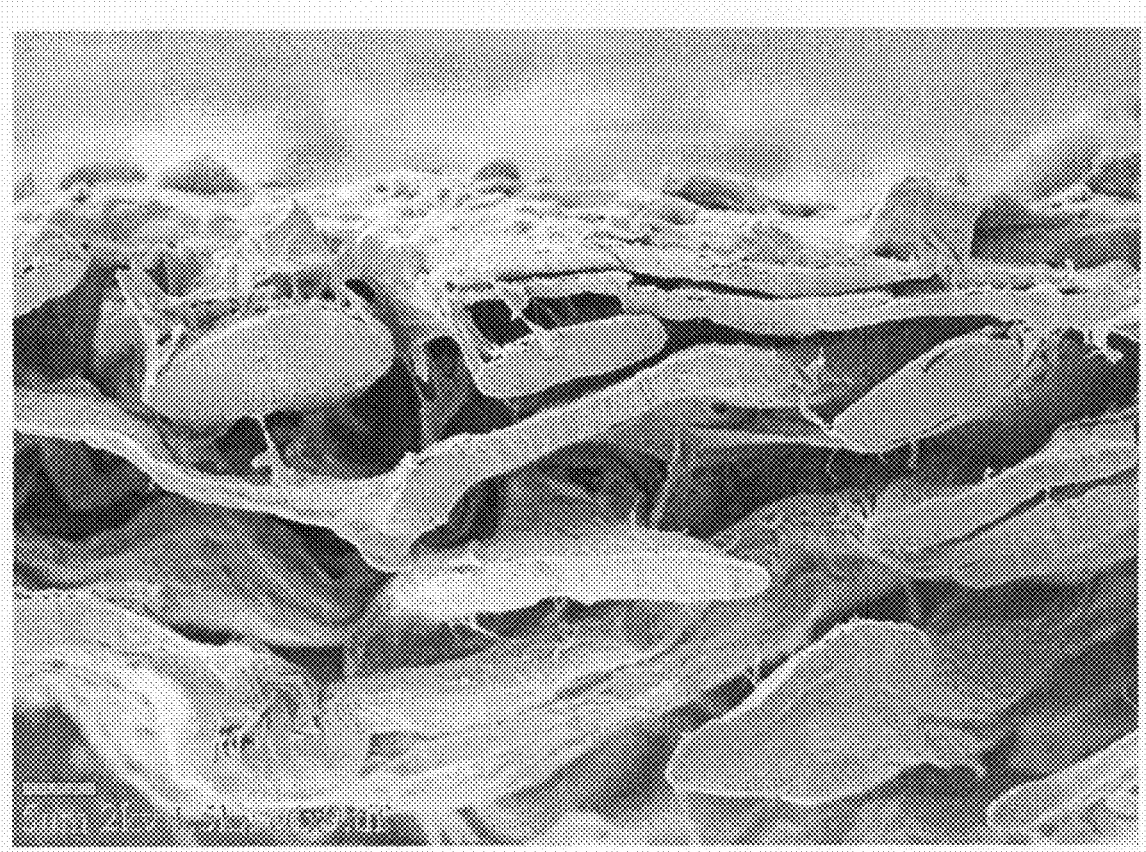

Referring to FIG. 12, a photograph of the cross section of the same sample illustrated in FIG. 9 is shown. As can be seen in the photograph, even at 10% solution solids, most of the additive composition remains on the surface of the tissue web. In this regard, the additive composition penetrates the web in an amount less than about 25% of the thickness of the web, such as less than about 15% of the thickness of the web, such as less than about 5% of the thickness of the web.

In this manner, it is believed that the additive composition provides a significant amount of strength to the tissue web. Further, because the film is discontinuous, the wicking properties of the web are not substantially adversely affected. Of particular advantage, these results are obtained without also a substantial increase in stiffness of the tissue web and without a substantial decrease in the perceived softness.

EXAMPLE 2

In this example, tissue webs made according to the present disclosure were compared to commercially available products. The samples were subjected to various tests. In particular, the samples were subjected to a "Stick-Slip Parameter Test" which measures the perceived softness of the product by measuring the spacial and temporal variation of a drag force as skin simulant is dragged over the surface of the sample.

More particularly, the following tests were performed in this example.

Stick-Slip Test

Stick-Slip occurs when the static coefficient of friction ("COF") is significantly higher than the kinetic COF. A sled pulled over a surface by a string will not move until the force in the string is high enough to overcome the static COF times the normal load. However, as soon as the sled starts to move the static COF gives way to the lower kinetic COF, so the pulling force in the string is unbalanced and the sled accelerates until the tension in the string is released and the sled stops (sticks). The tension then builds again until it is high enough to overcome the static COF, and so on. The frequency and amplitude of the oscillations depend upon the difference between the static COF and the kinetic COF, but also upon the length and stiffness of the string (a stiff, short string will let the force drop down almost immediately when the static COF is overcome so that the sled jerks forward only a small distance), and upon the speed of travel. Higher speeds tend to reduce Stick-Slip behavior.

Static COF is higher than kinetic COF because two surfaces in contact under a load tend to creep and comply with each other and increase the contact area between them. COF is proportional to contact area so more time in contact gives a higher COF. This helps explain why higher speeds give less Stick-Slip: there is less time after each slip event for the surfaces to comply and for the static COF to rise. For many materials the COF decreases with higher speed sliding because of this reduced time for compliance. However, some materials (typically soft or lubricated surfaces) actually show an increase in COF with increasing speed because the surfaces in contact tend to flow either plastically or viscoelastically and dissipate energy at a rate proportional to the rate at which they are sheared. Materials which have increasing COF with velocity do not show Stick-Slip because it would take more force to make the sled jerk forward than to continue at a constant slower rate. Such materials also have a static COF equal to their kinetic COF. Therefore, measuring the slope of the COF versus velocity curve is a good means of predicting whether a material is likely to show Stick-Slip: more negative slopes will Stick-Slip easily, while more positive slopes will not Stick-Slip even at very low velocities of sliding.

Figure 13:
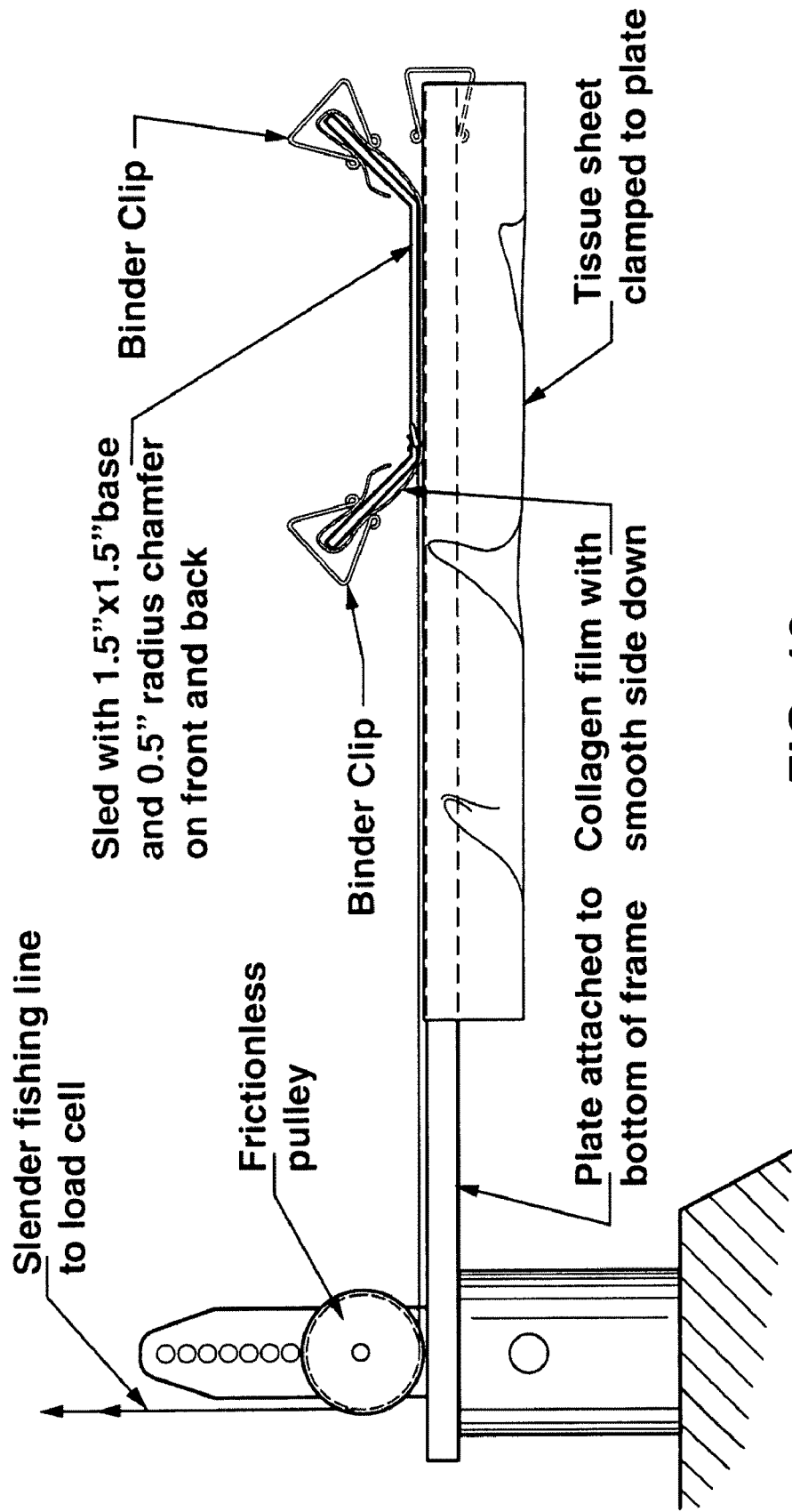
FIG. 13 is a diagram illustrating the equipment used to perform a Stick-Slip Test.

According to the Stick-Slip Test, the variation in COF with velocity of sliding is measured using an Alliance RT/1 tensile frame equipped with MTS TestWorks 4 software. A diagram of part of the testing apparatus is shown in FIG. 13. As illustrated, a plate is fixed to the lower part of the frame, and a tissue sheet (the sample) is clamped to this plate. An aluminum sled with a 1.5" by 1.5" flat surface with a 12" radius on the leading and trailing edges is attached to the upper (moving part) of the frame by means of a slender fishing line (30 lb, Stren clear monofilament from Remington Arms Inc, Madison, N.C.) lead though a nearly frictionless pulley up to a 50 N load cell. A 50.8 mm wide sheet of collagen film is clamped flat to the underside of the sled by means of 32 mm binder clips on the front and back of the sled. The total mass of the sled, film and clips is 81.1 g. The film is larger than the sled so that it fully covers the contacting surfaces. The collagen film may be obtained from NATURIN GmbH, Weinhein, Germany, under the designation of COFFI (Collagen Food Film), having a basis weight of 28 gsm. Another suitable film may be obtained from Viscofan USA Inc, 50 County Court, Montgomery Ala. 36105. The films are embossed with a small dot pattern. The flatter side of the film (with the dots dimpled down) should be facing down toward the tissue on the sled to maximize contact area between the tissue and collagen. The samples and the collagen film should be conditioned at 72 F and 50% RH for at least 6 hours prior to testing.

The tensile frame is programmed to drag the sled at a constant velocity (V) for a distance of 1 cm while the drag force is measured at a frequency of 100 hz. The average drag force measured between 0.2 cm and 0.9 cm is calculated, and kinetic COF is calculated as:

$$COF_V = \frac{f}{81.1} \quad (1)$$

Where f is the average drag force in grams, and 81.1 g is the mass of the sled, clips and film.

For each sample the COF is measured at 5, 10, 25, 50 and 100 cm/min. A new piece of collagen film is used for each sample.

The COF varies logarithmically with velocity, so that the data is described by the expression:

$$COF = a + SSP \ln(V)$$

Where a is the best fit COF at 1 cm/min and SSP is the Stick-Slip Parameter, showing how the COF varies with velocity. A higher value of SSP indicates a more lotiony, less prone to Stick-Slip sheet. SSP is measured for four tissue sheet samples for each code and the average is reported.

Hercules Size Test (HST)

The "Hercules Size Test" (HST) is a test that generally measures how long it takes for a liquid to travel through a tissue sheet. Hercules size testing was done in general accordance with TAPPI method T 530 PM-89, Size Test for Paper with Ink Resistance. Hercules Size Test data was collected on a Model HST tester using white and green calibration tiles and the black disk provided by the manufacturer. A 2% Napthol Green N dye diluted with distilled water to 1% was used as the dye. All materials are available from Hercules, Inc., Wilmington, Del.

All specimens were conditioned for at least 4 hours at 23+/−1 C and 50+/−2% relative humidity prior to testing. The test is sensitive to dye solution temperature so the dye solution should also be equilibrated to the controlled condition temperature for a minimum of 4 hours before testing.

Six (6) tissue sheets as commercially sold (18 plies for a 3-ply tissue product, 12 plies for a two-ply product, 6 plies for a single ply product, etc.) form the specimen for testing. Specimens are cut to an approximate dimension of 2.5×2.5 inches. The instrument is standardized with white and green calibration tiles per the manufacturer's directions. The specimen (12 plies for a 2-ply tissue product) is placed in the sample holder with the outer surface of the plies facing outward. The specimen is then clamped into the specimen holder. The specimen holder is then positioned in the retaining ring on top of the optical housing. Using the black disk, the instrument zero is calibrated. The black disk is removed and 10+/− 0.5 milliliters of dye solution is dispensed into the retaining ring and the timer started while placing the black disk back over the specimen. The test time in seconds (sec.) is recorded from the instrument.

Extraction Method for Determining Additive Content in Tissue

One method for measuring the amount of additive composition in a tissue sample is removal of the additive composition in a suitable solvent. Any suitable solvent may be selected, provided that it can dissolve at least a majority of the additive present in the tissue. One suitable solvent is Xylene.

To begin, a tissue sample containing the additive composition (3 grams of tissue minimum per test) was placed in an oven set at 105° C. overnight to remove all water. The dried tissue was then sealed in a metal can with a lid and allowed to cool in a dessicator containing calcium sulfate dessicant to prevent absorption of water from the air. After allowing the sample to cool for 10 minutes, the weight of the tissue was measured on a balance with an accuracy of ±0.0001 g. and the weight recorded ($W_1$).

The extraction was performed using a soxhlet extraction apparatus. The soxhlet extraction apparatus consisted of a 250 ml glass round bottom flask connected to a soxhlet extraction tube (Corning® no. 3740-M, with a capacity to top of siphon of 85 ml) and an Allihn condenser (Corning® no. 3840-MCO). The condenser was connected to a fresh cold water supply. The round bottom flask was heated from below using an electrically heated mantle (Glas Col, Terre Haute, Ind. USA) controlled by a variable auto transformer (Superior Electric Co., Bristol, Conn. USA).

To conduct an extraction, the pre-weighed tissue containing the additive composition was placed into a 33 mm×80 mm cellulose extraction thimble (Whatman International Ltd, Maidstone, England). The thimble was then put into the soxhlet extraction tube and the tube connected to the round bottom flask and the condenser. Inside the round bottom flask was 150 ml of xylene solvent. The heating mantle was energized and water flow through the condenser was initiated. The variable auto transformer heat control was adjusted such that the soxhlet tube filled with xylene and cycled back into the round bottom flask every 15 minutes. The extraction was conducted for a total of 5 hours (approximately 20 cycles of xylene through the soxhlet tube). Upon completion the thimble containing the tissue was removed from the soxhlet tube and allowed to dry in a hood. The tissue was then transported to an oven set at 150° C. and dried for 1 hour to remove excess xylene solvent. This oven was vented to a hood. The dry tissue was then placed in an oven set at 105° C. overnight. The next day the tissue was removed, placed in a metal can with a lid, and allowed to cool in a desiccator containing calcium sulfate desiccant for 10 minutes. The dry, cooled extracted tissue weight was then measured on a balance with an accuracy of ±0.0001 g. and the weight recorded ($W_2$).

The % xylene extractives was calculated using the equation below:

$$\% \text{ xylene extractives} = 100 \times (W_1 - W_2) * W_1$$

Because not all of the additive composition may extract in the selected solvent, it was necessary to construct a calibration curve to determine the amount of additive composition in an unknown sample. A calibration curve was developed by first applying a known amount of additive to the surface of a pre-weighed tissue ($T_1$) using an air brush. The additive composition was applied evenly over the tissue and allowed to dry in an oven at 105° C. overnight. The weight of the treated tissue was then measured ($T_2$) and the weight % of additive was calculated using the equation below:

$$\% \text{ additive} = 100 \times (T_2 - T_1) T_1$$

Treated tissues over a range of additive composition levels from 0% to 13% were produced and tested using the soxhlet extraction procedure previously described. The linear regression of % xylene extractives (Y variable) vs. % additive (X variable) was used as the calibration curve.

Calibration curve: % xylene extractives=m(% additive)+b or: % additive=(% xylene extractives−b)/m where: m=slope of linear regression equation
b=y-intercept of linear regression equation After a calibration curve has been established, the additive composition of a tissue sample can be determined. The xylene extractives content of a tissue sample was measured using the soxhlet extraction procedure previously described. The % additive in the tissue was then calculated using the linear regression equation:

$$\% \text{ additive} = (\% \text{ xylene extractives} - b)/m$$

where: m=slope of linear regression equation
b=y-intercept of linear regression equation A minimum of two measurements were made on each tissue sample and the arithmetic average was reported as the % additive content.

Dispersibility-Slosh Box Measurements

The slosh box used for the dynamic break-up of the samples consists of a 14"W×18"D×12"H plastic box constructed from 0.5" thick Plexiglas with a tightly fitting lid. The box rests on a platform, with one end attached to a hinge and the other end attached to a reciprocating cam. The amplitude of the rocking motion of the slosh box is ±2" (4" range). The speed of the sloshing action is variable but was set to a constant speed of 20 revolutions per minute of the cam, or 40 sloshes per minute. A volume of 2000 mL of either the "tap water" or "soft water" soak solution was added to the slosh box before testing. The tap water solution can contain about 112 ppm $HCO_3^-$, 66 ppm $Ca^{2+}$, 20 ppm $Mg^{2+}$, 65 ppm $Na^+$, 137 ppm $Cl^-$, 100 ppm $SO_4^{2-}$ with a total dissolved solids of 500 ppm and a calculated water hardness of about 248 ppm equivalents $CaCO_3$. The soft water solution, on the other hand, contains about 6.7 ppm $Ca^{2+}$, 3.3 ppm $Mg^{2+}$, and 21.5 ppm Cl with a total dissolved solids of 31.5 ppm and a calculated water hardness of about 30 ppm equivalents $CaCO_3$. A sample was unfolded and placed in the slosh box. The slosh box was started and timing was started once the sample was added to the soak solution. The break-up of the sample in the slosh box was visually observed and the time required for break-up into pieces less than about 1" square in area was recorded. At least three replicates of the samples were recorded and averaged to achieve the recorded values. Sample which do not break-up into pieces less than about 1" square in area within 24 h in a particular soak solution are considered non-dispersible in that soak solution by this test method.

In this example, 14 tissue samples were made and subjected to at least one of the above tests and compared to various commercially available tissue products.

The first three samples made according to the present disclosure (Sample Nos. 1, 2 and 3 in the table below) were made generally according to the process described in Example 1 above.

Tissue web samples 4 through 7, on the other hand, were made generally according to the process illustrated in FIG. 2. In order to adhere the tissue web to a creping surface, which in this embodiment comprised a Yankee dryer, additive compositions made according to the present disclosure were sprayed onto the dryer prior to contacting the dryer with the web. Two-ply or three-ply tissue products were produced. The samples were then subjected to various standardized tests.

Initially, softwood kraft (NSWK) pulp was dispersed in a pulper for 30 minutes at 4% consistency at about 100 degrees F. Then, the NSWK pulp was transferred to a dump chest and subsequently diluted to approximately 3% consistency. Then, the NSWK pulp was refined at 4.5 hp-days/metric ton. The above softwood fibers were utilized as the inner strength layer in a 3-layer tissue structure. The NSWK layer contributed approximately 34% of the final sheet weight.

Two kilograms KYMENE® 6500, available from Hercules, Incorporated, located in Wilmington, Del., U.S.A., per metric ton of wood fiber was added to the furnish prior to the headbox.

Aracruz ECF, a eucalyptus hardwood Kraft (EHWK) pulp available from Aracruz, located in Rio de Janeiro, RJ, Brazil, was dispersed in a pulper for 30 minutes at about 4% consistency at about 100 degrees Fahrenheit. The EHWK pulp was then transferred to a dump chest and subsequently diluted to about 3% consistency. The EHWK pulp fibers represent the two outer layers of the 3-layered tissue structure. The EHWK layers contributed approximately 66% of the final sheet weight.

Two kilograms KYMENE® 6500 per metric ton of wood fiber was added to the furnish prior to the headbox.

The pulp fibers from the machine chests were pumped to the headbox at a consistency of about 0.1%. Pulp fibers from each machine chest were sent through separate manifolds in the headbox to create a 3-layered tissue structure. The fibers were deposited onto a felt in a Crescent Former, similar to the process illustrated in FIG. 2.

The wet sheet, about 10-20% consistency, was adhered to a Yankee dryer, traveling at about 2500 fpm, (750 mpm) through a nip via a pressure roll. The consistency of the wet sheet after the pressure roll nip (post-pressure roll consistency or PPRC) was approximately 40%. The wet sheet adhered to the Yankee dryer due to the additive composition that is applied to the dryer surface. Spray booms situated underneath the Yankee dryer sprayed the additive composition, described in the present disclosure, onto the dryer surface at an addition level of 100 to 600 mg/m².

To prevent the felt from becoming contaminated by the additive composition, and to maintain desired sheet properties, a shield was positioned between the spray boom and the pressure roll.

The sheet was dried to about 95%-98% consistency as it traveled on the Yankee dryer and to the creping blade. The creping blade subsequently scraped the tissue sheet and a portion of the additive composition off the Yankee dryer. The creped tissue base sheet was then wound onto a core traveling at about 1970 fpm (600 mpm) into soft rolls for converting. The resulting tissue base sheet had an air-dried basis weight of 14.2 g/m². Two or three soft rolls of the creped tissue were then rewound and plied together so that both creped sides were on the outside of the 2- or 3-ply structure. Mechanical crimping on the edges of the structure held the plies together. The plied sheet was then slit on the edges to a standard width of approximately 8.5 inches and folded. Tissue samples were conditioned and tested.

The additive composition that was applied to Samples 4 through 7 and tested is as follows:

Quaternium-15) obtained from The Dow Chemical Company, was also present in each of the additive compositions.

The percent solids in solution for the different additive compositions was varied to deliver 100 to 600 mg/m² spray coverage on the Yankee Dryer. Varying the solids content in solution also varies the amount of solids incorporated into the base web. For instance, at 100 mg/m² spray coverage on the Yankee Dryer, it is estimated that about 1% additive composition solids is incorporated into the tissue web. At 200 mg/m² spray coverage on the Yankee Dryer, it is estimated that about 2% additive composition solids is incorporated into the tissue web. At 400 mg/m² spray coverage on the Yankee Dryer, it is estimated that about 4% additive composition solids is incorporated into the tissue web.

Tissue Sample No. 8, on the other hand, comprised a 2-ply product. Tissue Sample No. 8 was made similar to the process described in Example 1. The tissue web, however, was substantially dry prior to being attached to the dryer drum using the additive composition.

Prior to testing, all of the samples were conditioned according to TAPPI standards. In particular, the samples were placed

| Polymer (wt. ratios in parentheses) | Dispersing Agent | Dispersing Agent conc. (wt. %) |
|---|---|---|
| AFFINITY ™ EG8200/PRIMACOR ™ 5986 (60/40) | PRIMACOR ™ 5986 | 40.0 |

| Polymer Particle size (um) | Polydispersity | Solids (wt. %) | pH | Viscosity (cp) | Temp (o C.) | RPM | Spindle |
|---|---|---|---|---|---|---|---|
| 0.71 | 2.12 | 40.0 | 11.3 | 448 | 22.1 | 50 | RV3 |

DOWICIL™ 75 antimicrobial, which is a preservative with the active composition of 96% c is 1-(3-chloroallyl)-3,5,7-triaza-1-azoniaadamantane chloride (also known as in an atmosphere at 50% relative humidity and 72° F. for at least four hours.

The following results were obtained:

| Sample No. | Identification of Control Samples | # plies | Basis Weight - Bone Dry (gsm) | Basis Weight (gsm) | Additive Composition Coverage (mg/m²) | GMT (g/3") | GMT/Ply | HST (seconds) | xylene extraction add-on (%) | Dispersibility Slosh Box (min) | Stick-Slip Result |
|---|---|---|---|---|---|---|---|---|---|---|---|
| Control 1 | PUFF's Plus (Procter & Gamble) | 2 | | | 0 | | | | | | −0.020 |
| Control 2 | CELEB Glycerin Treated Tissue(Nepia) | 2 | | | 0 | | | | | | −0.019 |
| Control 3 | KLEENEX Ultra (Kimberly-Clark) | 3 | 39.21 | | 0 | 880 | 293 | 65.8 | | | −0.018 |
| Control 4 | PUFFS (Procter & Gamble) | 2 | | | 0 | 672 | 336 | | | | −0.018 |
| Control 5 | KLEENEX Lotion (Kimberly-Clark) | 3 | | | 0 | | | | | | −0.017 |
| Control 6 | KLEENEX (Kimberly-Clark) | 2 | 26.53 | | 0 | 622 | 311 | 1.2 | | | −0.012 |
| Control 7 | COTTONELLE Ultra (Kimberly-Clark) | 2 | | | 0 | | | | | 1.1 | −0.013 |
| Control 8 | ANDREX (Kimberly-Clark) | 2 | | | 0 | | | | | 0.1 | −0.017 |
| Control 9 | CHARMIN Ultra (Procter & Gamble) | 2 | | | 0 | | | | | 1.9 | −0.018 |
| Control 10 | CHARMIN Plus (Procter & Gamble) | 2 | | | 0 | | | | | | −0.018 |
| Control 11 | CHARMIN Giant (Procter & Gamble) | 1 | | | 0 | | | | | | −0.021 |
| 1 | | 2 | | | 2804 | | | 1.5 | 23.8 | | 0.058 |
| 2 | | 2 | | | 701 | 927 | 464 | | 6.8 | | 0.054 |
| 3 | | 2 | | | 1402 | 1170 | 585 | | 13.3 | | 0.070 |

-continued

| Sample No. | Identification of Control Samples | # plies | Basis Weight - Bone Dry (gsm) | Basis Weight (gsm) | Additive Composition Coverage (mg/m²) | GMT (g/3") | GMT/ Ply | HST (seconds) | xylene extraction add-on (%) | Dispersibility Slosh Box (min) | Stick-Slip Result |
|---|---|---|---|---|---|---|---|---|---|---|---|
| 4 | | 2 | 27.32 | | 200 | 792 | 396 | 4.1 | 1.2 | | 0.000 |
| 5 | | 2 | 26.89 | | 400 | 775 | 388 | 7 | 4.1 | | 0.016 |
| 6 | | 3 | 39.93 | | 400 | 1067 | 356 | 9.8 | 3.3 | | 0.018 |
| 7 | | 2 | | | 431 | 874 | 437 | | 3.2* | | 0.023 |
| 8 | | 2 | | 28 | 411 | 1457 | | 1.2 | 1.4 | 0.5 | −0.006 |

As shown above, the samples made according to the present disclosure had good water absorbency rates as shown by the Hercules Size Test. In particular, samples made according to the present disclosure had an HST of well below 60 seconds, such as below 30 seconds, such as below 20 seconds, such as below 10 seconds. In fact, two of the samples had an HST of less than about 2 seconds.

In addition to being very water absorbent, bath tissue samples made according to the present disclosure even containing the additive composition had good dispersibility characteristics. For instance, as shown, the sample tested had a dispersibility of less than about 2 minutes, such as less than about 1½ minutes, such as less than about 1 minute.

As also shown by the above table, samples made according to the present disclosure had superior Stick-Slip characteristics. As shown, samples made according to the present disclosure had a Stick-Slip of from about −0.007 to about 0.1. More particularly, samples made according to the present disclosure had a Stick-Slip of greater than about −0.006, such as greater than about 0. All of the comparative examples, on the other hand, had lower Stick-Slip numbers.

EXAMPLE 3

Tissue samples made according to the present disclosure were prepared similar to the process described in Example No. 2 above. In this example, the additive composition was applied to the first sample in a relatively heavy amount and to a second sample in a relatively light amount. In particular, Sample 1 contained the additive composition in an amount of 23.8% by weight. Sample 1 was made similar to the manner in which Sample 1 was produced in Example No. 4 above. Sample 2, on the other hand, contained the additive composition in an amount of about 1.2% by weight. Sample 2 was made generally in the same manner as Sample 4 was made in Example No. 2 above.

After the samples were prepared, one surface of each sample was photographed using a scanning electron microscope.

Figure 14:
Figure 15:
Figure 16:
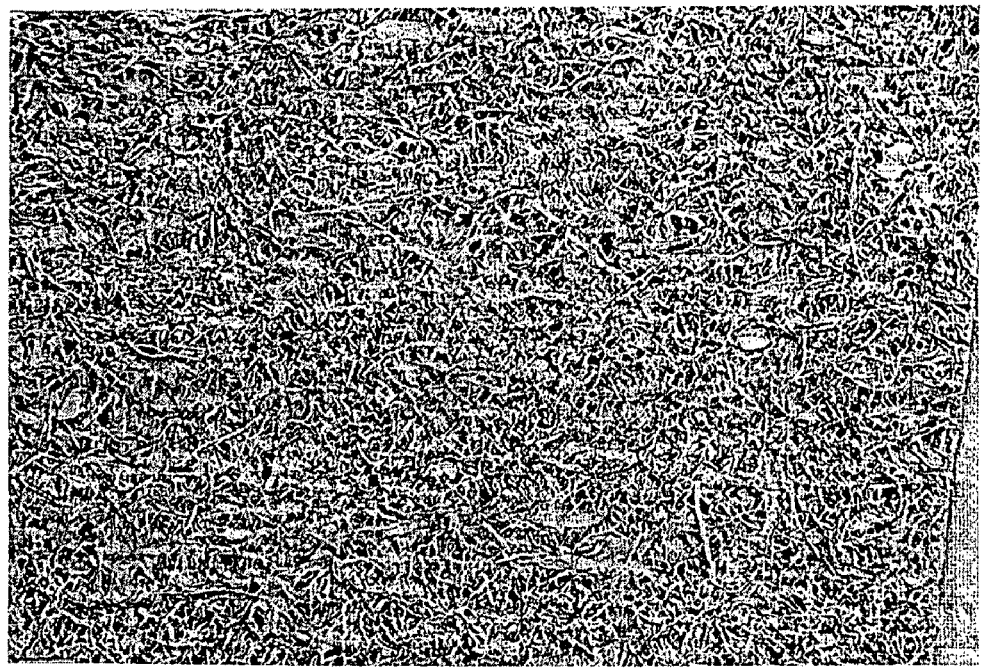
Figure 17:
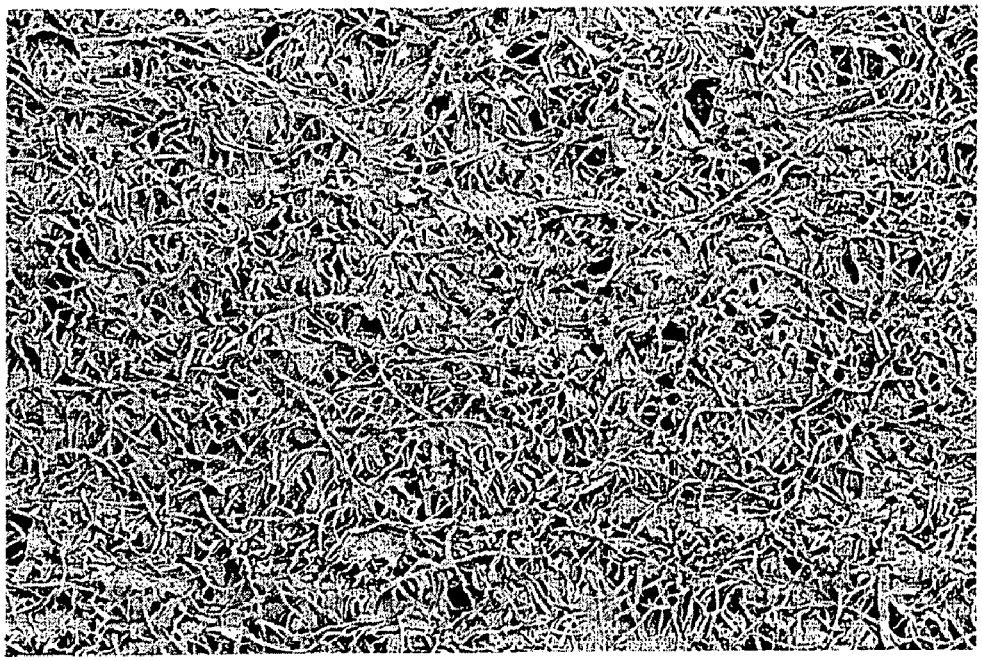
Figure 18:
Figure 19:
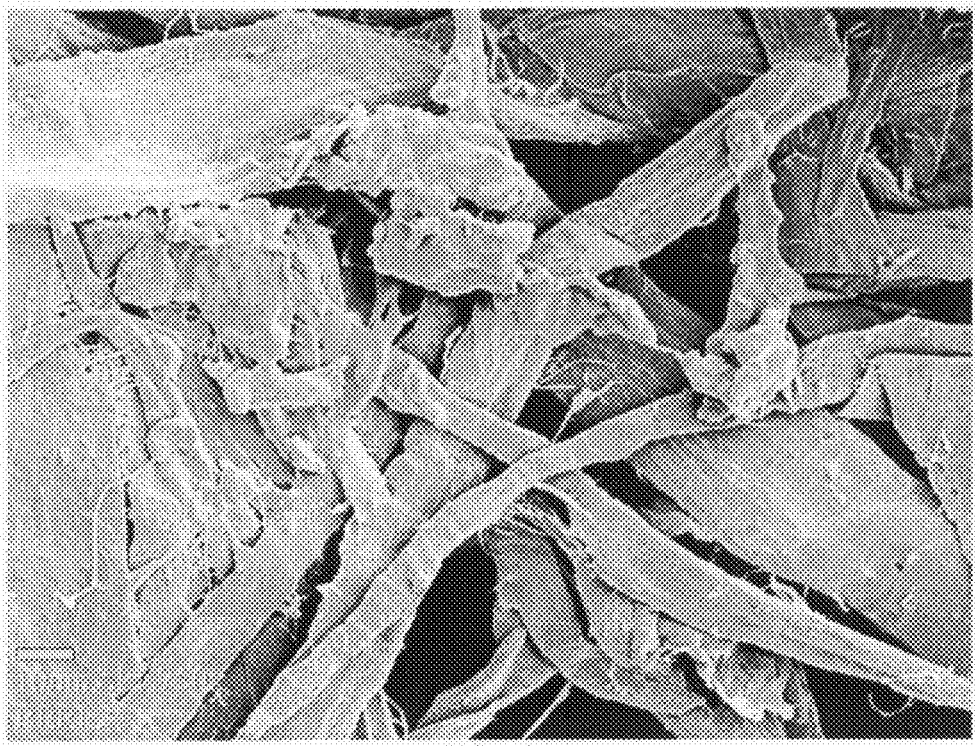

The first sample containing the additive composition in an amount of 23.8% by weight is illustrated in FIGS. 14 and 15. As shown, in this sample, the additive composition forms a discontinuous film over the surface of the product.

FIGS. 16-19, on the other hand, are photographs of the sample containing the additive composition in an amount of about 1.2% by weight. As shown, at relatively low amounts, the additive composition does not form an interconnected network. Instead, the additive composition is present on the surface of the product in discrete and separate areas. Even at the relatively low amounts, however, the tissue product still has a lotiony and soft feel These and other modifications and variations to the present disclosure may be practiced by those of ordinary skill in the art, without departing from the spirit and scope of the present disclosure, which is more particularly set forth in the appended claims. In addition, it should be understood that aspects of the various embodiments may be interchanged either in whole or in part. Furthermore, those of ordinary skill in the art will appreciate that the foregoing description is by way of example only, and is not intended to limit the disclosure so further described in such appended claims.

What is claimed:

1. A process for producing a sheet product comprising:
    applying an additive composition to a moving creping surface, the additive composition comprising an aqueous dispersion containing an alpha olefin interpolymer of ethylene or propylene and at least one comonomer, each comonomer being limited solely to compounds represented by the formula $H_2C{=}CHR$ where R is a $C_1$ to $C_{20}$ linear or branched alkyl group, wherein said aqueous dispersion has an average particle size in the range from 0.05 µm to 5 µm;
    pressing a base sheet against the creping surface after the additive composition has been applied, the additive composition adhering the base sheet to the creping surface; and
    removing the base sheet from the creping surface, wherein the additive composition transfers to the base sheet such that the additive composition comprises at least about 1% of the basis weight of the sheet product, the sheet product containing cellulosic fibers in an amount of at least 50% by weight and having a bulk of at least 3 cc/g.

2. A process as defined in claim 1, wherein the additive composition comprises from about 2% to about 50% of the basis weight of the sheet product.

3. A process as defined in claim 1, wherein the base sheet is creped from the creping surface.

4. A process as defined in claim 1, wherein the base sheet comprises at least about 80% by weight cellulosic fibers.

5. A process as defined in claim 1, wherein the base sheet comprises a wet laid tissue web.

6. A process as defined in claim 1, wherein the base sheet comprises an air formed web.

7. A process as defined in claim 1, wherein the base web comprises a spunbond web or a meltblown web.

8. A process as defined in claim 1, wherein the base sheet comprises a hydroentangled web, the base sheet containing synthetic fibers and cellulosic fibers.

9. A process as defined in claim 1, wherein the base sheet comprise a co-formed web, the web containing synthetic fibers and cellulosic fibers.

10. A process as defined in claim 1, wherein the base sheet has a consistency of from about 10% to about 30% when pressed against the creping surface.

11. A process as defined in claim 1, wherein the base sheet has a consistency of from about 30% to about 70% when pressed against the creping surface.

12. A process as defined in claim 1, wherein the base sheet contains moisture in an amount less than about 5% by weight when pressed against the creping surface.

13. A process as defined in claim 1, wherein the creping surface is heated to a temperature from about 20° C. to about 150° C.

14. A process as defined in claim 1, wherein the base sheet is on the creping surface for a period of time from about 120 milliseconds to about 2,000 milliseconds prior to being removed from the creping surface.

15. A process as defined in claim 1, wherein the creping surface comprises a surface of a rotating cylinder.

16. A process as defined in claim 1, wherein the additive composition comprises a lotion.

17. A process as defined in claim 1, wherein the additive composition further comprises an ethylene-carboxylic acid copolymer.

18. A process as defined in claim 17, wherein the olefin polymer comprises an interpolymer of ethylene and an alkene.

19. A process as defined in claim 17, wherein the additive composition further comprises a softener.

20. A process as defined in claim 17, wherein the additive composition further comprises a debonder.

21. A process as defined in claim 17, wherein the additive composition further comprises aloe, vitamin E, a wax, an oxidized polyethylene, or mixtures thereof.

22. A process as defined in claim 1, wherein the additive composition comprises from about 2% to about 30% of the basis weight of the sheet product.

23. A process as defined in claim 1, wherein the additive composition comprises from about 2% to about 15% of the basis weight of the sheet product.

24. A process as defined in claim 1, wherein the additive composition further comprises an adhesive.

25. A process as defined in claim 1, wherein the additive composition further comprises a latex polymer.

26. A process as defined in claim 24, wherein the adhesive comprises, an ethylene carbon monoxide polymer, a polyacrylate, a polyurethane, a starch, or mixtures thereof.

27. A process as defined in claim 16, wherein the additive composition comprises an adhesive.

28. A process as defined in claim 16, wherein the additive composition comprises a latex polymer.

29. A process as defined in claim 17, wherein the additive composition comprises an adhesive.

30. A process as defined in claim 17, wherein the additive composition comprises a latex polymer.

31. A process for producing a sheet product comprising:
applying an aqueous polyolefin dispersion to a moving creping surface, wherein said aqueous polyolefin dispersion comprises at least one thermoplastic resin, water, and at least one dispersing agent, wherein said aqueous polyolefin dispersion has an average particle size in the range of from 0.05 μm to 5 μm and a pH in a range of from 7 to 11, and wherein said dispersion comprises more than 25 percent by weight of water;
pressing a base sheet having an initial basis weight against the creping surface after the aqueous polyolefin dispersion has been applied, the aqueous polyolefin dispersion adhering the base sheet to the creping surface, wherein said base sheet comprises greater than 50 percent by weight of cellulosic materials and has a bulk greater than 3 cc/g; and
removing the base sheet from the creping surface, wherein the aqueous polyolefin dispersion transfers to the base sheet such that the basis weight of the base sheet increases by at least about 1 percent by weight.

32. A process as defined in claim 31, wherein the base sheet comprises a wet laid base web.

33. A process as defined in claim 31, wherein the base sheet comprises an air formed web.

34. A process as defined in claim 31, wherein the base web comprises a spunbond web or a meltblown web.

35. A process as defined in claim 31, wherein the base sheet comprises a hydroentangled web, the base sheet containing synthetic fibers and cellulosic fibers.

36. A process as defined in claim 31, wherein the base sheet comprises a co-formed web, the web containing synthetic fibers and cellulosic fibers.

37. A process as defined in claim 31, wherein the base sheet has a consistency of from 10 percent to 30 percent when pressed against the creping surface.

38. A process as defined in claim 31, wherein the base sheet has a consistency of from 30 percent to 70 percent when pressed against the creping surface.

39. A process as defined in claim 31, wherein the base sheet contains moisture in an amount less than about 5 percent by weight when pressed against the creping surface.

40. A process as defined in claim 31, wherein the creping surface is heated to a temperature from 70° C. to 350° C.

41. A process as defined in claim 31, wherein the base sheet is on the creping surface for a period of time from 120 milliseconds to 2,000 milliseconds prior to being removed from the creping surface.

42. A process as defined in claim 31, wherein the creping surface comprises a surface of a rotating cylinder.

43. A process as defined in claim 31, wherein said process further comprises the step of thereby forming an interconnected and discontinuous film on one surface of the base sheet.

44. A process as defined in claim 31, wherein said process further comprises the step of thereby forming treated discrete areas on the surface of said base sheet.

45. A process as defined in claim 44, wherein the aqueous polyolefin dispersion comprises an alpha-olefin interpolymer of ethylene and at least one comonomer selected from the group consisting of a $C_4$ to $C_{20}$ linear, branched or cyclic diene, vinyl acetate, and a compound represented by the formula $H_2C=CHR$, wherein R is a $C_1$ to $C_{20}$ linear, branched or cyclic alkyl group or a $C_6$ to $C_{20}$ aryl group, or the alpha-olefin polymer comprises a copolymer of propylene with at least one comonomer selected from the group consisting of ethylene, a $C_4$ to $C_{20}$ linear, branched or cyclic diene, and a compound represented by the formula $H_2C=CHR$, wherein R is a $C_1$ to $C_{20}$ linear, branched or cyclic alkyl group or a $C_6$ to $C_{20}$ aryl group.

46. A process as defined in claim 44, wherein the aqueous polyolefin dispersion comprises a mixture of an non-fibrous olefin polymer and an ethylene-carboxylic acid copolymer, and wherein the non-fibrous olefin polymer comprises an interpolymer of ethylene and an alkene, and wherein the aqueous dispersion further comprises a carboxylic acid.

47. A process as defined in claim 31, wherein the basis weight of the base sheet increases by from 2 percent to 30 percent by weight.

48. A process as defined in claim 31, wherein the basis weight of the base sheet increases by from 2 percent to 15 percent by weight.

49. A process as defined in claim 31, wherein the basis weight of the base sheet increases by from 2 percent to 50 percent by weight.

50. A process as defined in claim 31, wherein the base sheet is creped from the creping surface.

* * * * *